United States Patent
Kietzmann et al.

(10) Patent No.: US 11,103,632 B2
(45) Date of Patent: Aug. 31, 2021

(54) PACKAGING ASSEMBLY

(71) Applicant: Sanofi-Aventis Deutschland GMBH, Frankfurt am Main (DE)

(72) Inventors: Hardy Kietzmann, Frankfurt am Main (DE); Fred Luck, Frankfurt am Main (DE); Stefan Riebel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/779,657

(22) PCT Filed: Nov. 28, 2016

(86) PCT No.: PCT/EP2016/079040
§ 371 (c)(1),
(2) Date: May 29, 2018

(87) PCT Pub. No.: WO2017/093200
PCT Pub. Date: Jun. 8, 2017

(65) Prior Publication Data
US 2018/0256812 A1   Sep. 13, 2018

(30) Foreign Application Priority Data

Nov. 30, 2015  (EP) .................................. 15197093
Nov. 30, 2015  (EP) .................................. 15197097
Nov. 30, 2015  (EP) .................................. 15197101

(51) Int. Cl.
*G16H 20/17*  (2018.01)
*A61M 5/00*   (2006.01)
(Continued)

(52) U.S. Cl.
CPC ............ *A61M 5/002* (2013.01); *A61M 5/008* (2013.01); *A61M 5/3202* (2013.01); *A61J 7/0076* (2013.01); *A61M 2209/06* (2013.01)

(58) Field of Classification Search
CPC . G08B 21/185; A61M 15/00; A61M 15/0001; A61M 15/08; A61M 5/20;
(Continued)

(56) References Cited

U.S. PATENT DOCUMENTS 4,572,403 A * 2/1986 Benaroya .................. A61J 7/04
                                                        221/15
5,522,503 A    6/1996 Halbich
(Continued)

FOREIGN PATENT DOCUMENTS

CN      2568179      8/2003
CN      1630604      6/2005
(Continued)

OTHER PUBLICATIONS

International Preliminary Report on Patentability in International Application No. PCT/EP2016/079040, dated Jun. 5, 2018, 6 pages.
(Continued)

*Primary Examiner* — Hai Phan
*Assistant Examiner* — Anthony D Arifa-Kyei
(74) *Attorney, Agent, or Firm* — Fish & Richardson P.C.

(57) ABSTRACT

A packaging assembly includes a case configured to at least partially contain injection devices for delivering a medicament; a light sensor configured to detect light incident on the packaging assembly; and a status indicator configured to generate an output which indicates a status of the packaging assembly conditional on an intensity of light detected by the light sensor exceeding a threshold light intensity.

26 Claims, 12 Drawing Sheets

(51) Int. Cl.
*A61M 5/32* (2006.01)
*A61J 7/00* (2006.01)

(58) Field of Classification Search
CPC .... A61M 5/2035; A61M 5/31; A61M 5/3157; A61M 11/007; A61M 2005/206; A61M 2005/2073; A61M 2205/14; A61M 2205/18; A61M 2205/3306; A61M 2205/3375; A61M 2205/3553; A61M 2205/3561; A61M 2205/3569; A61M 2205/3584; A61M 2205/3592; A61M 2205/43; A61M 2205/50; A61M 2205/52; A61M 2205/581; A61M 2205/582; A61M 2205/583; A61M 2205/587; A61M 2205/8206; A61M 2205/8212; A61M 2230/04; A61M 2230/20; A61M 2230/201; A61M 2230/42; A61M 5/3202; A61M 5/5086; G06F 19/00; G06F 19/3468; G06F 19/3462; G09B 9/00; G16H 20/17; H04B 1/3827; H04W 4/008; H04W 4/80; Y02A 90/26; A61J 1/035; A61J 7/0418; A61J 7/0481; A61J 2200/30; A61J 2205/70; A61J 7/0436
See application file for complete search history.

(56) References Cited

U.S. PATENT DOCUMENTS

| | | | |
|---|---|---|---|
| 5,915,558 | A | 6/1999 | Girvetz |
| 5,970,974 | A | 10/1999 | Van der Linden et al. |
| 6,056,118 | A | 5/2000 | Hargus et al. |
| 6,464,506 | B1 | 10/2002 | Dickerson |
| 6,595,362 | B2 | 7/2003 | Penney et al. |
| 6,955,259 | B1 | 10/2005 | Jesse |
| 7,434,686 | B2 | 10/2008 | Prindle |
| 8,544,645 | B2 | 10/2013 | Edwards et al. |
| 8,584,486 | B1 | 11/2013 | Allard et al. |
| 9,311,452 | B2 | 4/2016 | Dickie et al. |
| 2002/0050462 | A1 | 5/2002 | Penney et al. |
| 2004/0069667 | A1* | 4/2004 | Tomellini ............ B65D 25/105 206/364 |
| 2007/0214812 | A1* | 9/2007 | Wagner ................ F25D 29/008 62/129 |
| 2007/0215782 | A1 | 9/2007 | Phung et al. |
| 2009/0115598 | A1 | 5/2009 | Carlson |
| 2009/0134181 | A1 | 5/2009 | Wachman et al. |
| 2012/0232520 | A1* | 9/2012 | Sloan ...................... G06F 19/00 604/504 |
| 2013/0002795 | A1* | 1/2013 | Shavelsky ................ A61J 7/04 348/14.01 |
| 2013/0289536 | A1 | 10/2013 | Croizat et al. |
| 2014/0252927 | A1 | 9/2014 | Denny et al. |
| 2015/0048100 | A1 | 2/2015 | Dickie et al. |
| 2015/0283341 | A1 | 10/2015 | Adams et al. |
| 2015/0317455 | A1 | 11/2015 | Lehmann et al. |
| 2015/0378314 | A1 | 12/2015 | Nakabayashi |
| 2016/0129182 | A1* | 5/2016 | Schuster ................ G16H 40/63 702/56 |
| 2016/0162832 | A1* | 6/2016 | Thompson ......... G06Q 10/0833 705/332 |
| 2016/0199592 | A1* | 7/2016 | Eggert ..................... A61M 5/24 604/506 |
| 2016/0232877 | A1 | 8/2016 | Cho et al. |
| 2016/0243318 | A1 | 8/2016 | Despa et al. |
| 2017/0056605 | A1* | 3/2017 | Kondo ................... G16H 20/17 |
| 2017/0087059 | A1 | 3/2017 | Rodriguez et al. |
| 2017/0368260 | A1 | 12/2017 | McCullough et al. |
| 2018/0015218 | A1 | 1/2018 | Welsch |

FOREIGN PATENT DOCUMENTS

| | | |
|---|---|---|
| CN | 2744339 | 12/2005 |
| CN | 101073533 | 11/2007 |
| CN | 101384237 | 3/2009 |
| CN | 201352126 | 11/2009 |
| CN | 201664175 | 12/2010 |
| CN | 201877103 | 6/2011 |
| CN | 102542176 | 7/2012 |
| CN | 202311770 | 7/2012 |
| CN | 203634510 | 6/2014 |
| CN | 104055678 | 9/2014 |
| CN | 204050542 | 12/2014 |
| CN | 204351461 | 5/2015 |
| CN | 204467263 | 7/2015 |
| CN | 204766326 | 11/2015 |
| CN | 204890775 | 12/2015 |
| DE | 20201026 | 4/2002 |
| DE | 10132869 | 10/2002 |
| EP | 2119423 | 11/2009 |
| EP | 3010660 | 4/2016 |
| EP | 3103493 | 12/2016 |
| EP | 3449575 | 3/2019 |
| GB | 2520054 | 5/2015 |
| JP | S51-93401 | 7/1976 |
| JP | 2002-504397 | 2/2002 |
| JP | 2008-114008 | 5/2008 |
| KR | 10-1564249 | 11/2015 |
| WO | WO 1999/043283 | 9/1999 |
| WO | WO 01/87739 | 11/2001 |
| WO | WO 2003/062091 | 7/2003 |
| WO | WO 2005/046559 | 5/2005 |
| WO | WO 2007/082543 | 7/2007 |
| WO | WO 2007/126851 | 11/2007 |
| WO | WO-2011054000 A1 * 5/2011 ............ A61J 7/0481 |
| WO | WO 2011/070329 | 6/2011 |
| WO | WO 2013/025520 | 2/2013 |
| WO | WO 2013/050342 | 4/2013 |
| WO | WO 2014/096146 | 6/2014 |
| WO | WO 2014/159933 | 10/2014 |
| WO | WO 2014/192888 | 12/2014 |
| WO | WO 2014/204958 | 12/2014 |
| WO | WO 2015/032715 | 3/2015 |
| WO | WO 2015/151900 | 10/2015 |
| WO | WO 2016/022760 | 2/2016 |
| WO | WO 2016/142726 | 9/2016 |
| WO | WO 2017/186402 | 11/2017 |
| WO | WO 2018/153945 | 8/2018 |
| WO | WO 2018/154033 | 8/2018 |
| WO | WO 2018/172858 | 9/2018 |

OTHER PUBLICATIONS

International Search Report and Written Opinion in International Application No. PCT/EP2016/079040, dated Feb. 6, 2017, 8 pages.
International Preliminary Report on Patentability in International Application No. PCT/EP2016/079039, dated Jun. 5, 2018, 7 pages.
International Search Report and Written Opinion in International Application No. PCT/EP2016/079039, dated Feb. 21, 2017, 9 pages.
International Preliminary Report on Patentability in International Application No. PCT/EP2018/054464, dated Aug. 27, 2019, 7 pages.
International Search Report and Written Opinion in International Application No. PCT/EP2018/054464, dated May 23, 2018, 10 pages.
International Preliminary Report on Patentability in International Application No. PCT/EP2018/054323, dated Aug. 27, 2019, 7 pages.
International Search Report and Written Opinion in International Application No. PCT/EP2018/054323, dated May 4, 2018, 11 pages.
International Preliminary Report on Patentability in International Application No. PCT/EP2016/079038, dated Jun. 5, 2018, 7 pages.
International Search Report and Written Opinion in International Application No. PCT/EP2016/079038, dated Feb. 17, 2017, 10 pages.

* cited by examiner

PACKAGING ASSEMBLY

CROSS REFERENCE TO RELATED APPLICATIONS

The present application is the national stage entry of International Patent Application No. PCT/EP2016/079040, filed on Nov. 28, 2016, and claims priority to Application No. EP 15197093.6, filed on Nov. 30, 2015; Application No. EP 15197097.7, filed on Nov. 30, 2015; and Application No. EP 15197101.7, filed on Nov. 30, 2015, the disclosures of which are expressly incorporated herein in entirety by reference thereto.

FIELD

The application relates to a packaging assembly for a medicament and, in particular, although not exclusively, to a packaging assembly configured to provide a reminder alert at a scheduled dosing time.

BACKGROUND

Patients suffering chronic disease require regular treatment with medicaments, e.g. on the basis of a predefined schedule. Particular medicaments require refrigerated storage, and are often stored refrigerated in a household refrigerator or fridge. In a home treatment environment, the patient stores the medicament in their fridge and administers a predefined dose as required. Hence, the medicament is typically provided in a secondary packaging for convenient placement and storage in the household fridge. However, the medicament must be stored together with other items that require constant refrigeration, such as foodstuffs and beverages.

Depending on the dosage form of the medicament, the secondary packaging containing the medicament may store a primary packed medicament itself, or may store one or more different kinds of drug delivery devices. For instance, the medicament may be provided in a pre-filled syringe or pen-type injector.

A medicament may have a predefined dosing schedule which requires the administration of a dose at relatively long intervals, for instance every two or four weeks, or once a month. The medicament may be provided in a secondary packaging containing several doses which may be stored in the fridge for 1 to 6 months for instance. It can be difficult for patients to keep track of each scheduled dosing time.

SUMMARY

According to an embodiment, a packaging assembly is provided including a case configured to at least partially contain a plurality of injection devices for delivering a medicament; a lid coupled to the case and movable between an open position and a closed position; a countdown timer configured to monitor a time remaining to a scheduled time; a sensor configured to output a signal representative of a change in position of the lid from the closed position to the open position; and a reminder alert configured to activate once the scheduled time has been reached, and deactivate based on the signal received from the sensor.

The packaging assembly may include an audio output transducer; wherein the reminder alert is an audio output generated by the audio output transducer.

The packaging assembly may include an optical transducer; wherein the optical transducer is configured to generate a visual reminder output at the scheduled time.

The optical transducer may be configured to generate the visual reminder output when the lid is in the closed position and when the lid is in the open position.

The optical transducer may include a display; wherein the display is configured to generate an output to show an amount of time remaining until the scheduled time; and wherein the display is configured to generate the visual reminder output once the scheduled time has been reached.

The display may be configured to generate an output to show a number of days remaining until the scheduled time.

The display may be configured to show the number of days remaining until the scheduled time continuously, if the number of days remaining is greater than one day, and to show the number of days remaining until the scheduled time intermittently, if the number of days remaining is equal to or less than one day.

The display may be configured to generate an output which indicates that a state of charge of batteries included in the packaging assembly is below a threshold state of charge.

The display may be configured to generate the output to indicate the low state of charge by showing a battery low message output alternately with the output to show the amount of time remaining until the scheduled time.

The optical transducer may include a notification light; wherein the packaging assembly is configured to intermittently activate the notification light once the scheduled time has been reached to generate the visual reminder output.

The packaging assembly may include a light sensor configured to detect an amount of light incident on the packaging assembly; wherein the optical transducer is configured to generate an output conditional on an intensity of light detected by the light sensor exceeding a threshold light intensity.

The packaging assembly may include a door open timer configured to be started in response to detecting that the intensity of light sensed by the light sensor exceeds the threshold light intensity, wherein the optical transducer is configured to generate the visual output only if the door open timer has not expired.

The door open timer may be configured to expire after a predetermined time in the range of 1 minute to 10 minutes.

The lid may be arranged to cover the optical transducer in the closed position.

The lid may be translucent.

At least a portion of the lid may be transparent.

The packaging assembly may include a reset input device and the packaging assembly may be configured to respond to operation of the reset input device by a user to set the scheduled time.

The packaging assembly may be configured to respond to operation of the reset input device by a user to set the scheduled time to 14 days.

The packaging assembly may be configured to respond to operation of the reset input device by a user to set the scheduled time to 28 days.

The sensor may be an electromechanical switch arranged within the packaging assembly such that the state of the electromechanical switch changes between open and closed states as the lid is moved from the closed position to the open position.

The electromechanical switch may be arranged within the packaging assembly such that contact between the switch and a component of a hinge assembly changes as the lid is moved from the closed position to the open position.

The packaging assembly may include at least one injection device including a medicament.

According to another aspect, a packaging assembly is provided including a case configured to at least partially contain a plurality of injection devices for delivering a medicament; a light sensor configured to detect light incident on the packaging assembly; and a status indicator configured to generate an output which indicates a status of the packaging assembly conditional on an intensity of light detected by the light sensor exceeding a threshold light intensity.

The packaging assembly may include a countdown timer configured to monitor a time remaining to a scheduled time; wherein the status indicator is configured to generate an output which indicates a status of the countdown timer.

The packaging assembly may include a reset input device and the packaging assembly may be configured to respond to operation of the reset input device by a user to set the scheduled time.

The packaging assembly may be configured to respond to operation of the reset input device by a user to set the scheduled time to 14 days.

The packaging assembly may be configured to respond to operation of the reset input device by a user to set the scheduled time to 28 days.

The status indicator may include an audio output transducer; wherein the audio output transducer is configured to generate an audio reminder output to indicate that the scheduled time has been reached conditional on the intensity of light detected by the light sensor exceeding the threshold light intensity.

The status indicator may include an optical transducer; wherein the optical transducer is configured to generate a visual output to indicate the status of the countdown timer.

The optical transducer may include a notification light; wherein the notification light is activated at the scheduled time to generate a visual reminder output conditional on the intensity of light detected by the light sensor exceeding the threshold light intensity.

The optical transducer may include a display; wherein the display is configured to generate an output to show a number of days remaining until the scheduled time.

The display may be configured to show the number of days remaining until the scheduled time continuously, if the scheduled time has not been reached, and to show the number of days remaining until the scheduled time intermittently, when the scheduled time has been reached.

The packaging assembly may include a door open timer configured to be started in response to detecting that the intensity of light sensed by the light sensor exceeds the threshold amount of light, wherein the optical transducer is configured to generate the visual output only if the door open timer has not expired.

The door open timer may be configured to expire after a predetermined time in the range of 1 minute to 10 minutes.

The status indicator may be configured to generate an output which indicates that a state of charge of batteries included in the packaging assembly is below a threshold state of charge.

The packaging assembly may include a lid coupled to the case and movable between open and closed positions; and a sensor configured to output a signal representative of a change in position of the lid from the closed position to the open position.

At least one output of the status indicator may be configured to deactivate based on the signal received from the sensor.

The status indicator may be configured to generate a further output based on the signal received from the sensor, the further output providing information relating to the status of the packaging assembly.

The lid may be translucent.

At least a portion of the lid may be transparent.

The sensor may be an electromechanical switch arranged within the packaging assembly such that the state of the electromechanical switch changes between open and closed states as the lid is moved from the closed position to the open position.

The electromagnetic switch may be arranged within the packaging assembly such that contact between the electromechanical switch and a component of a hinge assembly changes as the lid is moved from the closed position to the open position.

The packaging assembly may include at least one injection device including a medicament.

According to another aspect, a method of operating a packaging assembly configured to receive a plurality of injection devices is provided, including determining a time remaining to a scheduled time to remove one of the plurality of injection devices from the packaging assembly; receiving a signal from a sensor representative of a change in position of a lid of the packaging apparatus; activating a reminder alert once the scheduled time has been reached; and deactivating the reminder alert based on the signal received from the sensor.

The reminder alert may be an audio output.

The method may include generating a visual output comprising a visual reminder output generated at the scheduled time.

Generating the visual output may include generating the visual reminder output when the lid is in the closed position and when the lid is in the open position.

Generating the visual output may include generating an output to show a number of days remaining until the scheduled time.

Generating the visual output may include generating the output to show the number of days remaining until the scheduled time continuously, if the number of days remaining is greater than one day, and generating the output to show the number of days remaining until the scheduled time intermittently, if the number of days remaining is equal to or less than one day.

Generating the visual output further may include generating an output which indicates that a state of charge of batteries included in the packaging assembly is below a threshold state of charge.

Generating the visual output may include generating the output to indicate the low state of charge by showing a battery low message output alternately with the output to show the number of days remaining until the scheduled time.

Generating the visual reminder output may include intermittently activating a notification light once the scheduled time has been reached.

The method may include receiving a signal from a light sensor representative of an intensity of light incident on the packaging assembly; wherein the generating the visual output comprises generating the visual output conditional on an intensity of light incident on the packaging assembly exceeding a threshold light intensity.

The method may include starting a door open timer in response to detecting that the intensity of light incident on the packaging assembly exceeds the threshold light intensity; wherein generating the visual output comprises generating the visual output only if the door open timer has not expired.

The door open timer may be configured to expire after a predetermined time in the range of 1 minute to 10 minutes.

The method may include receiving a signal from a reset input device; and setting the scheduled time in response to receiving the signal from the reset input device.

Setting the scheduled time may include setting the scheduled time to 14 days.

Setting the scheduled time may include setting the scheduled time to 28 days.

According to another aspect, a method of operating a packaging assembly is provided, including receiving a signal from a light sensor representative of an intensity of light incident on the packaging assembly; and generating an output which indicates a status of the packaging assembly conditional on the intensity of light incident on the packaging assembly exceeding a threshold light intensity.

The method may include determining a time remaining to a scheduled time; wherein generating an output comprises generating an output which indicates a status of the countdown timer.

The method may include receiving a signal from a reset input device; and setting the scheduled time in response to receiving the signal from the reset input device.

Setting the scheduled time may include setting the scheduled time to 14 days.

Setting the scheduled time may include setting the scheduled time to 28 days.

Generating the output may include generating an audio reminder output to indicate that the scheduled time has been reached conditional on the intensity of light incident on the packaging assembly exceeding the threshold light intensity.

Generating the output may include generating a visual output to indicate the status of the countdown timer.

Generating the visual output may include activating a notification light at the scheduled time to generate a visual reminder output conditional on the intensity of light incident on the packaging assembly exceeding the threshold light intensity.

The method may include starting a door open timer in response to detecting that the intensity of light incident on the packaging assembly exceeds the threshold amount of light; wherein generating the output comprises generating the output only if the door open timer has not expired.

The door open timer may be configured to expire after a predetermined time in the range of 1 minute to 10 minutes.

Generating the output may include generating an output which indicates that a state of charge of batteries included in the packaging assembly is below a threshold state of charge.

The method may include receiving a signal from a sensor representative of a change in position of a lid of the packaging assembly from a closed position to an open position; and deactivating at least a part of the generated output based on the signal received from the sensor.

Generating the output may include generating a further output based on the signal received from the sensor, the further output providing information relating to the status of the packaging assembly.

According to another aspect, a method of operating a packaging assembly is provided, including opening a refrigerator in which the packaging assembly is stored; and in response to a reminder alert output by the packaging assembly: opening a lid of the packaging assembly; removing an injection device from the packaging assembly for the administration of a medicament; and setting a scheduled time of the packaging assembly.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION

Figure 1:
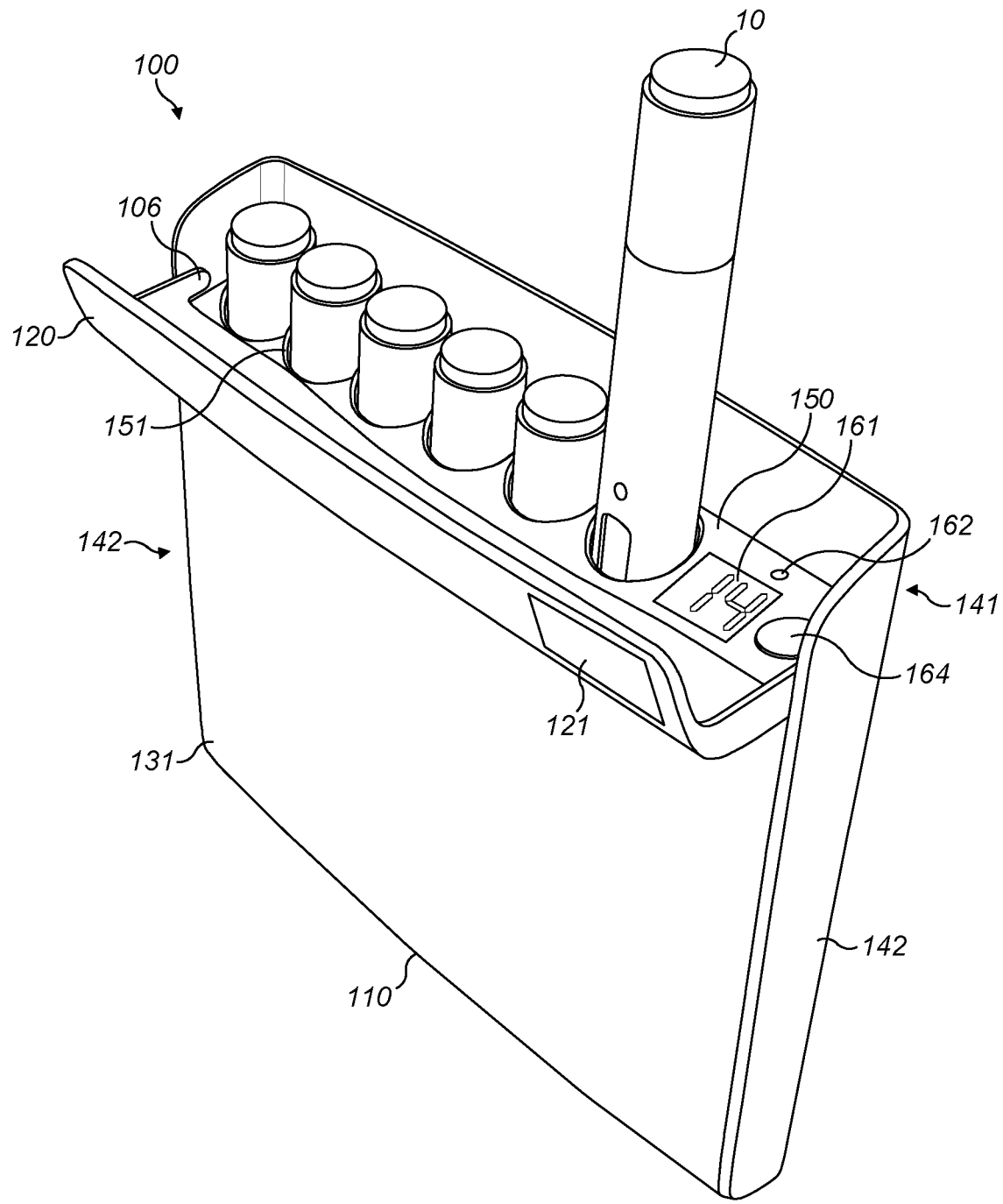
FIG. 1 is an isometric view of a packaging assembly according to a first exemplary embodiment.

Embodiments of the disclosure provide a packaging assembly configured to contain and store a plurality of injection devices for delivering a medicament. An injection device is an example of a drug delivery device and may be a pen-injector or an auto-injector. The packaging assembly is configured to provide an audio and/or visual reminder to a patient at a scheduled dosing time for the medicament. The packaging assembly may further include one or more user interface elements for providing the patient with a status and information relating to a status of the packaging assembly. The packaging assembly provides a predictable, easy to use operation for the patient.

The packaging assembly may be stored in a household refrigerator or fridge. The packaging assembly may include a door open sensor to determine whether or not the fridge is open. The packaging assembly may be configured to provide the reminder or a user interface output conditional on the fridge door being open. The packaging assembly provides information easily and intuitively, and allows safe storage in a fridge for convenient and discreet use by the patient.

The packaging assembly may determine whether or not the packaging assembly has been opened. The packaging assembly may deactivate the reminder upon detection of the packaging assembly being opened. The operation of the packaging assembly is predictable and intuitive for the patient.

A drug delivery device, as described herein, may be configured to inject a medicament into a patient. For example, delivery could be sub-cutaneous, intra-muscular, or intravenous. Such an injection device could be operated by a patient or care-giver, such as a nurse or physician, and can include various types of safety syringe, pen-injector, or auto-injector. The injection device can include a cartridge-based system that requires piercing a sealed ampule before use. Volumes of medicament delivered with these various injection devices can range from about 0.2 ml to about 3 ml. Yet another injection device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described injection devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, an injection device will often include a hollow needle ranging from about 25 to about 31 Gauge in size. Common sizes are 27 and 29 Gauge.

The injection devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 2:
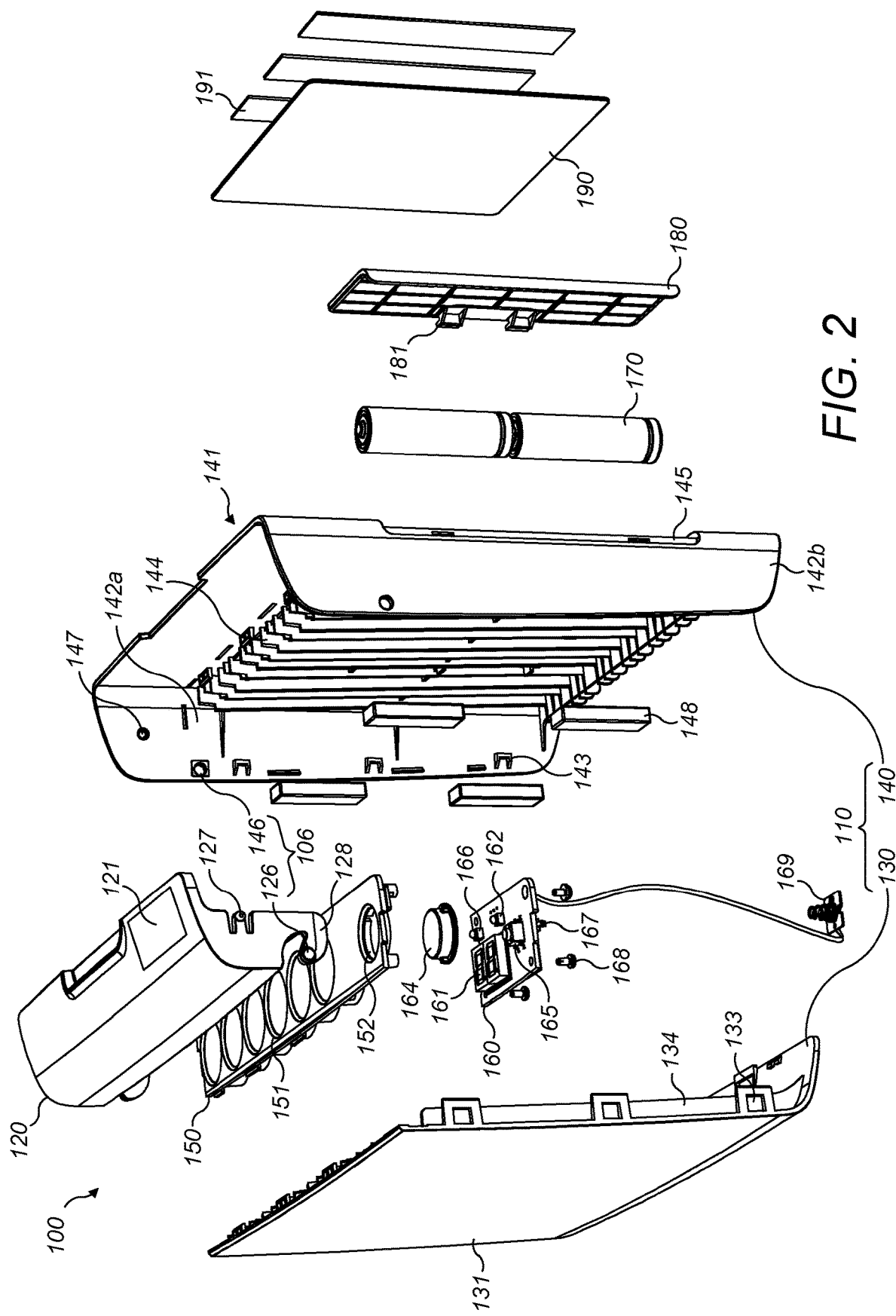
FIG. 2 is an exploded view of the packaging assembly of FIG. 1.

With reference to FIGS. 1 and 2, a packaging assembly 100 according to exemplary embodiments is shown. The packaging assembly 100 comprises a case 110 having a lid 120. The case 110 comprises a front face 130, a rear face 141, and two side walls 142. The front face 131 is curved so as to meet the rear face 141 at a base of the device. At an upper end of the case 110, an opening is formed between front face 131, the rear face 141 and the two side walls 142.

The lid 120 of the case 110 is arranged to cover the opening of the case 110. The lid 120 is attached between the two side walls 142 of the case 110 in a hinged manner. The lid 120 can be freely moved in a hinged manner between a closed position and an open position. In the closed position, the lid 120 is arranged to cover the opening of the case 110. In the open position, the opening of the case 110 is uncovered and an interior of the case 110 can be accessed.

The lid 120 may comprise a latching mechanism to hold the lid 120 in the closed position. The latching mechanism may comprise a protruding part arranged at an edge of the lid 120. The protruding part may be configured to engage with a corresponding feature in the case 110 when the lid is in the closed position. The protruding part may be flexible or retractable to disengage from the case 110 and allow the lid 120 to move to the open position.

The case 110 is configured to hold and store a plurality of injection devices 10. A height of the case 110, measured between the base and the lid 120, is sufficient to accommodate the length of each of the injection devices 10. The height of the case may be between 160 mm and 180 mm. A depth of the case 110, measured between the front face 131 and the rear face 141, is sufficient to accommodate the width of each of the injection devices 10. The depth of the case may be between 30 mm and 40 mm. A width of the case 110, measured between the two side walls 142, is sufficient to accommodate six injection devices 10. The width of the case may be between 180 mm and 200 mm. In some examples, the case may be 188.7 mm wide, 174.7 mm high and 34 mm deep.

As shown in FIG. 1, the front face 131 of the case 110 is shorter than the rear face 141. The lid 120 extends from a top edge of the front face 131 to a top edge of the rear face 141. The lid 120 is curved. The curve allows the lid 120 to form the top and a portion of the front of the case 110 in the closed position. Other lid configurations are also contemplated.

The front face 131, the rear face 141 and the two side walls 142 are formed from an opaque material, for example, an opaque plastic material. The lid 120 is formed from a translucent or frosted material, for example, a clear plastic material with a frosted coating or a treated surface. A portion of the lid 120 is clear and transparent to form a viewing window 121 through the lid 120.

The case 110 further comprises a panel 150 arranged within the opening. The panel 150 is visible only when the lid 120 of the case 110 is in an open position; when the lid 120 is in the closed position, the lid obscures the panel 150 from view. The panel 150 comprises a plurality of openings 151. The openings 151 are configured to hold a corresponding plurality of injection devices 10. The openings 151 in the panel 150 are circular in shape. The openings 151 may be square shaped, or rectangular shaped to accommodate other sizes of injection device 10. The width of each opening is sufficient to accommodate the width of each injection device 10. The panel 150 comprises a row of six openings, so as to hold six injection devices 10 arranged in a row along a width of the case 110. The packaging assembly 100 may be configured to hold more than six, or fewer than six injection devices 10 in the case 110.

The lid 120 may be configured to retain the plurality of injection devices 10 in position within the case 110 when in the closed position. The lid 120 may be arranged in the closed position to prevent the injection devices 10 from falling or sliding out of the case 110. Each injection device 10 may be retained in position within the corresponding opening 151 by a friction fit with the opening 151.

A retention mechanism may retain the plurality of injection devices 10 in position within the openings 151. The retention mechanism may comprise a mechanical catch configured to engage with each injection device 10, for example, a sprung push-catch push-release mechanism. The injection device 10 is pushed into the opening 151 and pushed against a spring of the retention mechanism to engage a catch, The injection device 10 is pushed a second time to release the catch. A release button or switch may be provided for each of the openings 151, which is configured to release the catch of the retention mechanism when pressed.

A user may receive the packaging assembly 100 in an empty condition. When the user is supplied with a plurality of injection devices 10 they can be loaded into the packaging assembly 100. The lid 120 is moved into the open position and each of the injection devices 10 is inserted into a corresponding one of the openings 151. The lid 120 is moved into the closed position. The packaging assembly 100 is placed in the fridge until the first scheduled dosing time is due.

For example, a dosing time may be scheduled every 14 days or 28 days, according to the form of medicament provided in the plurality of injection devices 10. In some embodiments, a period of time between scheduled dosing times may be between 2 days and 60 days, according to the requirements of the medicament.

The packaging assembly 100 is configured to provide the user with a visual and/or reminder when the scheduled dosing time is due. The packaging assembly 100 is further configured to determine whether or not the fridge door is open, and to provide the reminder conditional on the fridge door being open. The packaging assembly 100 is further configured to determine whether the lid 120 is in the open position or the closed position, and to deactivate the reminder upon detection of the lid 120 being moved to the open position. Functionality of the packaging assembly 100 is provided by the following electronics.

The packaging assembly 100 includes an electronics system 160 (not visible in FIG. 1, but visible in FIG. 2). The electronics system comprises multiple components that are connected together to provide a specific set of functions, described below. The components of the electronics system 160 are mounted on a printed circuit board (PCB), although instead they may be interconnected through some other medium.

The electronics system 160 is attached to the panel 150. Some of the electronic components of the electronics system 160 are user interface hardware components and together provide a user interface. The components that provide the user interface are positioned at one end of the row of openings 151 of the panel 150.

Figure 4:
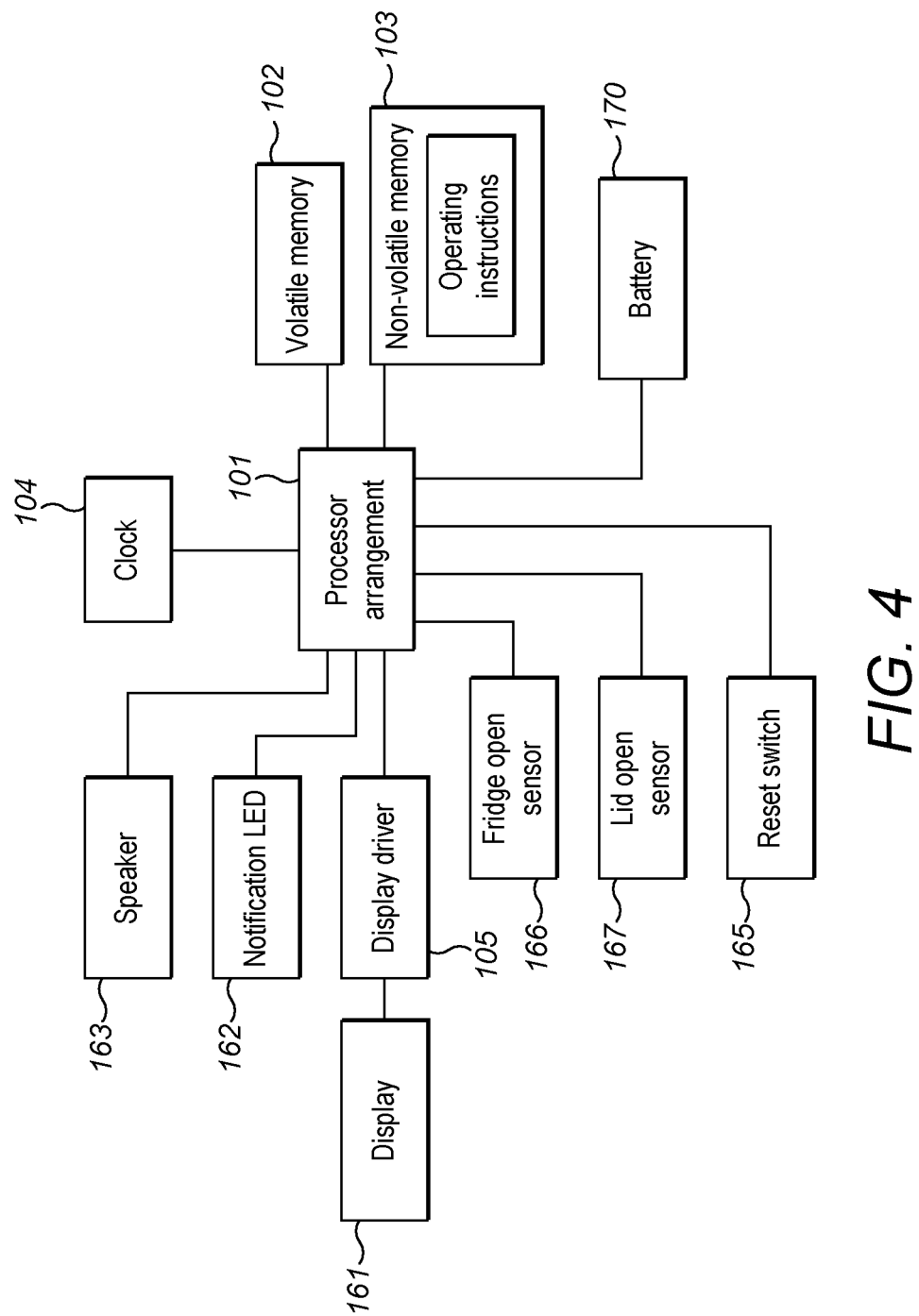
FIG. 4 is a block diagram of an electronics system of the packaging assembly, according to an exemplary embodiment.

The electronics system 160 is shown schematically in FIG. 4. The electronics system 160 comprises a processor arrangement 101, which is shown in FIG. 4. The processor arrangement 101 controls operation of the other hardware components of the electronics system 160. The processor arrangement 101 is configured to control the hardware components which form the user interface. The processor arrangement 101 is configured to process one or more input signals from at least one input sensor.

The electronics system 160 comprises a display 161. The display 161 is an example of an optical transducer. The display 161 comprises two seven-segment light-emitting diode (LED) arrays. The display 161 is visible to the user through the transparent viewing window 121 in the lid 120. The electronics system 160 comprises a light-emitting diode (LED) 162. The LED 162 is an example of an optical transducer. A colour of the LED 162 is different to a colour of the seven-segment LED arrays in the display 161, for example, the colour of the LED 162 is red and the colour of the display 161 is blue. The electronics system 160 comprises a reset button 164. The reset button 164 is an example of an input device. The reset button 164 is a sprung plunger button which may be depressed by the user. The electronics system 160 comprises a speaker 163 (not shown in this Figure). The speaker 163 is an example of an audio transducer.

With further reference to FIG. 2, an exploded view of the packaging assembly 100 according to the first embodiment is shown. The case 110 of the packaging assembly 100 comprises a first part 130 and a second part 140. The first part 130 of the case 110 is formed from a single piece. The first part 130 of the case 110 comprises the front face 131 and the base of the packaging assembly 100. Along each side edge of the front face 131, a plurality of openings 133 are formed for engaging with the second part 140 of the case 110. Three openings 133 are formed along each edge of the first part 130. The first part 130 further comprises a plurality of dividers 134 for holding the plurality of injection devices 10 (not shown in FIG. 2) in position within the case 110.

The second part 140 comprises the rear face 141, a first side wall 142a and a second side wall 142b of the case 110. The second part 140 is formed from a single piece. The second part 140 further comprises a plurality of dividers 144 for holding and storing the plurality of injection devices 10 in position within the case 110. The dividers 144 of the second part 140 are aligned with the dividers 134 of the first part 130.

The case 110 of the packaging assembly 100 comprises a plurality of magnets 148. The magnets 148 are fixed in position on an internal side of the rear face 141. The case comprises four magnets 148 fixed in a square arrangement. The plurality of magnets 148 allows the rear face 141 of the case 110 to be releasably attached to a magnetic surface, for example, a steel surface. The magnets 148 may be neodymium magnets.

The packaging assembly 100 further comprises a mounting plate 190. The mounting plate 190 comprises a plurality of adhesive strips 191. The mounting plate 190 can be fixed to a surface using the adhesive strips 191, such as, for example, a wall or under a shelf within a fridge. The mounting plate 190 is formed from a magnetic material, for example, steel. The case 110 can be releasable attached to the surface by magnetically attaching to the mounting plate 190.

The mounting plate 190 comprises three adhesive strips 191. The adhesive strips 191 are arranged in parallel across the width of the mounting plate 190 and each adhesive strip 191 extends along substantially the full length of the mounting plate. Alternatively, the mounting plate 190 may comprise only two adhesive strips 191 which are spaced apart on the mounting plate 190, or may comprise more than three adhesive strips 191 extending in parallel. Further alternatively, the mounting plate 190 may comprise four adhesive strips 191 positioned in a rectangular arrangement, for example, at each corner of the mounting plate 190. The mounting plate may comprise any number of adhesive strips 191 arranged in a regular array.

The mounting plate 190 may alternatively be placed, without adhesive, on an upper side of a shelf. The case 110 may be magnetically held beneath the shelf through a magnetic attraction to the mounting plate 190.

The packaging assembly 100 further comprises a plurality of batteries 170. The batteries 170 are arranged to provide power to the components of the user interface. The second part 140 of the case 110 comprises a battery opening 145 formed in the rear face 141. The battery opening 145 is configured to receive the plurality of batteries 170. A battery cover 180 is configured to slidably engage with the battery opening 145 of the second part 140 and to cover the battery opening 145 when the packaging assembly 100 is in use. The battery cover 180 comprises a plurality of latches 181 arranged to engage with the second part 140 of the case 110.

Each of the first side wall 142a and the second side wall 142b of the case 110 comprises a plurality of engaging hooks 143. The engaging hooks 143 are arranged on an inner face of the respective side wall. Each of the side walls 142 comprises three engaging hooks 143. The engaging hooks 143 are each configured to engage with the corresponding opening 133 in the first part 130 of the case 110. Each of the side walls 142 comprises a first hinging part 146. Each of the side walls 142 comprises a first latching part 147.

The lid 120 of the case 110 comprises a second hinging part 126 configured to engage with the first hinging part 146 of the second part 140 of the case 110. The first hinging part 146 and the second hinging part 126 together form a hinge 106 for attaching the lid 120 to the second part 140 of the case 110. For example, the first hinging part 146 comprises an opening and the second hinging part 126 comprises a protrusion arranged to fit within the opening of the first hinging part 146. The second hinging part 126 is configured to rotate within the opening of the first hinging part 146.

The lid 120 of the case 110 comprises a second latching part 127 configured to engage with the first latching part 147 of the second part 140 of the case 110. The second latching part 127 is configured to releasably engage with the first latching part 147 to maintain the lid 120 in a closed position. For example, the first latching part 147 comprises an opening and the second latching part 127 comprises a protrusion configured to releasably engage with the opening of the first latching part 147.

The lid 120 is formed from a translucent plastic material. A portion of the lid 120 is clear and transparent to form a viewing window 121 through the lid 120.

The panel 150 is held in position between the first part 130 and the second part 140 of the case 110. The panel 150 comprises the plurality of openings 151. The openings 151 are configured to hold the corresponding plurality of injection devices 10. The panel 150 further comprises one or more openings 152 for the hardware components of the user interface. The packaging assembly 100 comprises the electronics system 160. The electronics system 160 includes the hardware components of the user interface, namely the display 161, the LED 162, the speaker 163 and the reset button 164. The display 161 of the user interface is visible through the transparent viewing window 121 of the lid 120.

A plurality of screws 168 are arranged to attach a support of the electronics system 160, for instance a PCB, to a rear face 141 of the panel 150. The electronics system 160 is coupled with a battery contact 169. The battery contact 169 is mounted with the plurality of batteries 170 in order to supply power to the electronics system 160.

The electronics system 160 comprises a reset switch 165. The reset button 164 is a sprung plunger button arranged to be pushed by the user. The reset switch 165 is a mechanical switch mounted on the electronics system 160. The reset switch 165 is positioned below the reset button 164. The reset switch 165 is arranged to be actuated by the reset button 164. The reset button 164 may be coupled to the reset switch 165.

The electronics system 160 comprises a light sensor 166 mounted on the electronics system 160. The light sensor 166 comprises a phototransistor configured to pass a current according to the amount or intensity of light which is incident on the light sensor 166. The light sensor 166 is an example of a fridge open sensor.

The light sensor 166 may be of the type where the inherent device characteristics are such that an intensity of light exceeding a threshold results in a signal of one type (e.g. high) and an intensity of light below the threshold results in a signal of an opposite type (e.g. low). Alternatively, comparison of the intensity to a threshold may be performed by electronic components that are separate to the device of the light sensor 166 but form part of the light sensor itself. Here, the light sensitive device provides a signal with a level that varies according to the detected light intensity and the electronic components perform analysis of the signal compared to a threshold.

Further alternatively, the comparison may be performed in the digital domain by the processor arrangement 101. Here, the light sensor provides a signal with a level that varies according to the detected light intensity, this is converted by an analogue to digital converter (if not already a digital signal) and the processor arrangement compares the signal to a threshold. Unless the threshold is inherent in the device, the threshold may be preset (that is, predetermined and set at the design or manufacture stage) or it may be dynamically adjustable having regard to operating conditions.

The arrangement may be configured to filter out short duration bursts of light exceeding the threshold, which filtering may occur through the use of slow response components, so as to reduce the occurrence of false triggering. As will be appreciated, if there is false triggering from short duration periods of light intensity exceeding the threshold, the result is short duration activation of user interface components.

The electronics system 160 comprises a hinge switch 167. The hinge switch 167 may be an electro-mechanical switch such as a microswitch or other miniature snap action switch. The hinge switch 167 is an example of a lid open sensor.

The hinge switch 167 is arranged to engage with the lid 120 of the case 110 when the lid 120 is in a closed position. An actuating part 128 of the lid 120 is shaped so as to press the hinge switch 167 when the lid 120 is in a closed position. The hinge switch 167 is mounted at an edge of the PCB of the electronics system 160. The actuating part 128 of the lid 120 is arranged to pass the edge of the PCB of the electronics system 160 when the lid 120 is in a closed position.

The electronics system 160 further comprises the processor arrangement 101 (not shown in this Figure). The processor arrangement 101 is configured to process the input signals from the one or more sensors and the switches on the electronics system 160. The processor arrangement 101 is configured to control the outputs of the user interface elements on the electronics system 160.

Figure 3:
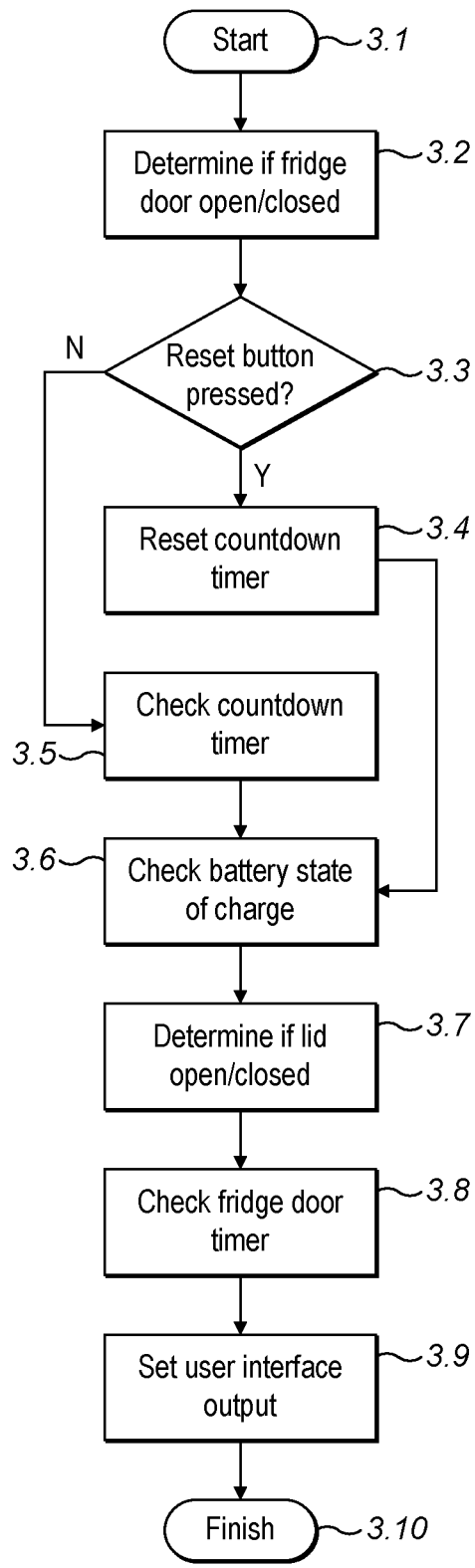
FIG. 3 is a flowchart illustrating a first exemplary operation of the packaging assembly, according to an exemplary embodiment.

A first exemplary operation of the packaging assembly 100 will now be described with reference to the flow chart of FIG. 3. In the following, actions said to be made by the packaging assembly 100 typically are made by the electronics system 160 and, in particular, by the processor arrangement 101 operating according to instructions to control the components of the electronics system 160. The flow chart of FIG. 3 is schematic.

The operation starts at step 3.1.

At step 3.2, the processor arrangement 101 determines whether a fridge door of a fridge in which the packaging assembly 100 is stored is open or closed. If the fridge door is partially open, then the processor arrangement 101 determines the fridge door to be open. That is, the fridge door is determined to be open if it is not closed. If the fridge door is determined to be open, the operation proceeds to step 3.3. Otherwise, it stays at step 3.2 until the fridge door is determined to be open. The user interface can be controlled by the processor arrangement 101 according to whether the fridge door is detected to be open or closed.

At step 3.3, the processor arrangement 101 checks whether or not the reset button 164 is pressed, that is to say whether it is currently being operated by a user. If the reset button 164 is pressed, the processor arrangement 101 proceeds to step 3.4. At step 3.4, a countdown timer of the processor arrangement 101 is reset. The processor arrangement 101 then proceeds to step 3.6.

If the reset button 164 is not determined to be pressed at step 3.3, the processor arrangement 101 proceeds to step 3.5. At step 3.5, the processor arrangement checks the countdown timer. The processor arrangement 101 can determine the time remaining (e.g. the number of days remaining) until the scheduled dosing time. The user interface can be controlled by the processor arrangement 101 according to whether or not the reset button 164 is pressed, and/or according to the countdown timer of the processor arrangement 101.

At step 3.6, the processor arrangement 101 checks the state of charge of one or more batteries 170 included in the packaging assembly 100. The user interface can be controlled by the processor arrangement 101 according to the state of change of the battery 170.

At step 3.7, the processor arrangement 101 determines whether the lid 120 of the packaging assembly 100 is in the open position or the closed position. The user interface can be controlled by the processor arrangement 101 according to whether or not the lid 120 is open.

At step 3.8, the processor arrangement 101 checks a door open timer. The processor arrangement 101 monitors the amount of time that the door of the fridge has been open using the door open timer. The user interface can be controlled by the processor arrangement 101 according to the door open timer of the processor arrangement 101.

At step 3.9, the processor arrangement 101 controls the hardware components of the electronics system 160 which form the user interface. The user interface is controlled based on the determinations made at any of steps 3.2, 3.3, 3.5, 3.6, 3.7 and 3.8

The packaging assembly 100 is configured to output a reminder alert if the scheduled dosing time is due. The packaging assembly 100 is configured to output the reminder alert conditional on the door of the fridge being open. The packaging assembly 100 is configured to deactivate the reminder alert upon detection of the lid 120 being moved from the closed position to the open position. The packaging assembly 11 is configured to enter a partial sleep state when the amount of time measured by the door timer is over a threshold time.

The packaging assembly 100 is configured to output an indication if the state of charge of one or more batteries 170 included in the packaging assembly 100 is low.

The operation finishes at step 3.10.

With respect to FIG. 4, a schematic representation of the electronics system 160 of the packaging assembly 100 according to the first embodiment is shown. The electronics system 160 comprises the processor arrangement 101. The processor arrangement 101 and other hardware components may be connected via a system bus (not shown). Each hardware component may be connected to the system bus either directly or via an interface. A battery 170 is arranged to provide power to the electronics system 160.

The processor arrangement 101 controls operation of the other hardware components of the electronics system 160. The processor arrangement 101 may be an integrated circuit of any kind. The processor arrangement 101 may for instance be a general purpose processor. It may be a single core device or a multiple core device. The processor arrangement 101 may be a central processing unit (CPU) or a general processing unit (GPU). Alternatively, it may be a more specialist unit, for instance a RISC processor or programmable hardware with embedded firmware. Multiple processors may be included. The processor arrangement 101 may be termed processing means.

The processor arrangement 101 has a clock speed of 2 Hz. The clock speed is selected to provide a balance between power usage and usability. A greater clock speed provides improved usability by reducing the time required for the processor arrangement 101 to respond to an input. However, a greater clock speed will increase the power usage of the processor arrangement 101. The clock speed may be selected between 0.5 and 100 Hz.

The electronics system 160 comprises a working or volatile memory 102. The processor arrangement 101 may access the volatile memory 102 in order to process data and may control the storage of data in memory. The volatile memory 102 may be a RAM of any type, for example Static RAM (SRAM), Dynamic RAM (DRAM), or it may be Flash memory. Multiple volatile memories may be included, but are omitted from the Figure.

The electronics system 160 comprises a non-volatile memory 103. The non-volatile memory 103 stores a set of operation instructions for controlling the normal operation of the processor arrangement 101. The non-volatile memory 103 may be a memory of any kind such as a Read Only Memory (ROM), a Flash memory or a magnetic drive memory. Other non-volatile memories may be included, but are omitted from the Figure.

The processor arrangement 101 operates under the control of the operating instructions. The operating instructions may comprise code (i.e. drivers) relating to the hardware components of the electronics system 160, as well as code relating to the basic operation of the packaging apparatus. The operating instructions may also cause activation of one or more software modules stored in the non-volatile memory 103. Generally speaking, the processor arrangement 101 executes one or more instructions of the operating instructions, which are stored permanently or semi-permanently in the non-volatile memory 103, using the volatile memory 102 temporarily to store data generated during execution of the operating instructions.

The processor arrangement 101, the volatile memory 102 and the non-volatile memory 103 may be provided as separate integrated circuit chips connected by an off-chip bus, or they may be provided on a single integrated circuit chip. The processor arrangement 101, the volatile memory 102 and the non-volatile memory 103 may be provided as a microcontroller.

The electronics system 160 comprises a clock 104. The clock 104 may be a clock crystal, for example, a quartz crystal oscillator. The clock 104 may be a separate component to the processor arrangement 101 which is configured to provide a clock signal to the processor arrangement 101. The processor arrangement 101 may be configured to provide a real time clock based on the signal from the clock 104. Alternatively, the clock 104 may be a clock crystal which is provide on a single integrated circuit chip with the processor arrangement 101.

The processor arrangement 101 is configured to perform a countdown operation. The countdown operation monitors a number of days remaining until the scheduled dosing time. The countdown operation is set and activated in response to an input from the reset switch 165. The predetermined time period for the countdown to the next scheduled dosing time is stored in the non-volatile memory with the operating instructions of the processor arrangement 101. The processor arrangement 101 records the number of days to the volatile memory 102 and every 24 hours reduces the recorded number of days by one.

For example, if the predetermined time period until the next scheduled dosing time is due is 14 days, the countdown operation is started from 14 days.

The electronics system 160 may comprise a timer duration switch. The timer duration switch may be configured to select the time period until the next scheduled dosing time. The timer duration switch may be a slide switch having a first position and a second position. The processor arrangement 101 may be configured to set the time period for the countdown to the next scheduled dosing time based on the position of the timer duration switch. The processor arrangement 101 may set the time period to be 14 days if the slide switch is in the first position. The processor arrangement 101 may set the time period to be 28 days if the slide switch is in the second position.

The position of the timer duration switch may be preset as part of a manufacturing process and may not be adjustable by a user. Alternatively, the timer duration switch may be accessible for a user to set the timer period to the next scheduled dosing time. The timer duration switch may be mounted on a rear face of the PCB of the electronics system. The timer duration switch may be accessible through the battery opening 145.

Every 24 hours, the number of days recorded to the volatile memory 102 is reduced by one. After 13 days, when 1 day remains until the scheduled dosing time, the processor arrangement 101 may control the electronics system 160 to generate an output to indicate that the scheduled dosing time is near. After 14 days, on the day of the scheduled dosing time, the processor arrangement 101 may control the electronics system 160 to generate an output to indicate that the scheduled dosing time is due. The hardware components of the electronics system 160 which form the user interface may be controlled to indicate that the scheduled dosing time is due.

On one day, for instance the first day, the reduction of the number of days may be provided in less than 24 hours. For instance, it may be achieved in 20 hours or 22 hours. This can help to prevent creep of the alert time to later and later in the day after multiple resets of the countdown timer. Alternatively, when the remaining number of days recorded in the volatile memory is equal to one, the processor arrangement 101 may be configured to reduce the time remaining until the next scheduled dosing time is due. For example, the processor arrangement 101 may be configured to wait only 23 hours before reducing the number of days to zero. In this way, the time of day at which the scheduled dosing time becomes due is one hour earlier than the time at which the reset button 164 was pressed.

The processor arrangement 101 may be configured to perform one or more timing operations. For example, the processor arrangement 101 may operate a door timer to monitor the amount of time that the door of the fridge has been open. The processor arrangement 101 may operate a reset timer to monitor the amount of time that the reset button 164 has been pressed. The processor arrangement 101 may start a timing operation from zero and monitor an increasing amount of time. Alternatively, the processor arrangement 101 may start a timing operation from a predetermined time and count down until the timer expires.

The processor arrangement 101 may be configured to check the state of charge of one or more batteries 170 included in the packaging assembly 100. The state of charge is determined to be low if it is below a threshold (which may be built into the design of the packaging arrangement). The state of charge may be determined by measurement of the voltage provided by the battery 170, by monitoring energy use from a full state of charge, or a combination of these two techniques.

The electronics system 160 comprises a fridge open sensor 166. The fridge open sensor 166 may be a light sensor, for example a phototransistor, mounted on the electronics system 160. The fridge open sensor 166 is configured to provide a signal to the processor arrangement 101 when light is incident on the phototransistor. For example, when the packaging assembly 100 is stored within a fridge, the fridge open sensor 166 may provide an indication that a door of the fridge is open by providing a signal when ambient light from outside the fridge, or light from an internal fridge light, is incident on the phototransistor. When the fridge door is closed, no light is incident on the phototransistor and the fridge open sensor 166 provides no signal or a small signal.

The fridge open sensor 166 may comprise a phototransistor configured to pass a current according to the amount or intensity of light which is incident on the phototransistor. The fridge open sensor 166 may be configured to provide a signal of one type (e.g. high) when an intensity of incident light exceeds a threshold, and a signal of an opposite type (e.g. low) when an intensity of incident light is below the threshold.

Alternatively, the fridge open sensor 166 provides a current signal to the processor arrangement 101 according to the intensity of light which is incident on the phototransistor. The received signal may be compared to a threshold by the processor arrangement 101. The threshold may be a preset threshold stored in the non-volatile memory 103, or it may be dynamically adjustable having regard to operating conditions.

The processor arrangement 101 is configured to determine whether a door of a fridge in which the packaging assembly 100 is stored is open or closed, based on a signal received from the fridge open sensor 166.

The processor arrangement 101 is configured to start a door timer when the fridge door is opened. The processor arrangement 101 starts the door open timer in response to a signal from the light sensor 166 to indicate that the fridge door is open. After the timer has been started, the device can be said to be in a door open state. The processor arrangement 101 may be configured to enter a partial sleep state when the time period measured by the door timer is over a threshold time. For example, the processor arrangement 101 may enter a partial sleep state when the fridge door has been open for 5 minutes. The door open timer may be configured to expire after a predetermined time, for instance in the range of 1 minute to 10 minutes. The processor arrangement 101 may control the electronics system 160 not to generate an output in the partial sleep state.

The device transitions from the door open state to the partial sleep state when the door timer passes the 5 minutes mark. The door timer may be started at 5 minutes when the door is detected to be opened and count down such that the timer expires if the door is not closed within 5 minutes.

The electronics system 160 comprises a lid open sensor. The lid open sensor 167 is configured to provide a signal to the processor arrangement 101 when the lid 120 of the case 110 in a closed position.

The lid open sensor 167 may be a hinge switch, for example an electro-mechanical switch such as a microswitch or other miniature snap action switch. The lid open sensor 167 may be arranged to mechanically engage with the lid 120 when the lid 120 is in a closed position. An actuating part 128 of the lid 120 may be shaped to engage with the lid open sensor 167 when the lid 120 is in a closed position. The lid open sensor 167 may be a normally open switch having an open state and a closed state. The switch may be operated to move from the open state to the closed state when pressed. The switch may be configured to pass a current in a closed state only.

The lid open sensor 167 may be configured to provide a signal to the processor arrangement 101 when the switch is pressed into the closed state by the lid 120. The processor arrangement 101 may be configured to set a variable to indicate whether or not the lid 120 has been opened. The processor arrangement 101 may store a lid flag. The processor arrangement 101 may set the lid flag to have a value of 1 when the lid open sensor 167 indicates that the lid 120 has been opened.

The electronics system 160 comprises a reset switch 165. The reset switch 165 is configured to provide a signal to the processor arrangement 101 when actuated by the reset button 164. The user presses the reset button 164 to indicate that the scheduled dosage has taken place, and to reset the time period for the next scheduled dosing time.

The reset switch 165 may be a mechanical switch mounted on the electronics system 160. The reset switch 165 is arranged to be actuated by the reset button 164. The reset switch 165 may be a normally open switch having an open state and a closed state. The reset switch 165 may be operated to move from the open state to the closed state when pressed. The reset switch 165 may be configured to pass a current in a closed state only. The reset switch 165 may be configured to provide a signal to the processor arrangement 101 when moved to the closed state.

The reset button 164 may be coupled to the reset switch 165. The reset switch 165 may be positioned below the reset button 164. If the reset button 164 is pressed, the reset switch 165 may be moved to the closed state by the reset button 164. The reset switch 165 is configured to provide a signal to the processor arrangement 101 when actuated by the reset button 164. The processor arrangement 101 is configured to reset the countdown operation in response to the signal from the reset switch 165. The time remaining until the scheduled dosing time is due is reset to be 14 days by the processor arrangement 101. The processor arrangement 101 may set the lid flag to have a value of 0 when the reset button 164 is pressed.

The processor arrangement 101 is configured to operate a reset timer. The processor arrangement 101 is configured to reset the time period for the next scheduled dosing time when the time period measured by the reset timer is over 2 seconds. The reset timer is started from zero when the reset switch 165 is moved to the closed state. Alternatively, the reset timer may be started at 2 seconds when the reset switch 165 is closed and count down such that the timer expires if the reset switch is not opened within 2 seconds.

The user must press and hold the reset button 164 for 2 seconds to maintain the reset switch 165 in the closed state for 2 seconds. The processor arrangement 101 is configured to reset the time period for the next scheduled dosing time if the user holds the reset button 164 for 2 seconds. The packaging assembly 11 filters out short presses of the reset button 164, so as to reduce the occurrence of falsely triggering the reset operation.

The electronics system 160 comprises the display 161 of the user interface. The display 161 can be operated to provide a notification. The display 161 can be operated to provide an indication of a status of the packaging assembly 100. The display 161 is an example of a status indicator. The display 161 can be operated to show information relating to the status of the packaging assembly 100. The display 161 can be operated to show any number from 00 to 99 by illuminating some or all of the LED segments. Certain letters may also be shown by the display 161.

The electronics system 106 may comprise a display driver 105. The display driver 105 may be provided as a separate integrated circuit chip to the processor arrangement 101, which is connected by an off-chip bus. Alternatively, the display driver 105 may be provided on a single integrated circuit chip with the processor arrangement 101. The display driver 105 may be a port expander for individually controlling the segments of a seven-segment LED display.

The processor arrangement 101 can operate the display 161 to show the number of days remaining until the scheduled dosing time is due. The display 161 can be operated to provide a visual reminder output that the scheduled dosing time is due. The display 161 can be operated further to provide a visual reminder output that the scheduled dosing time is near.

If the countdown operation of the processor arrangement 101 is reset, the countdown operation is started from 14 days. The display 161 is operated to show the number "14" to indicate that 14 days remain. Each day, the number of days shown by the display 161 is reduced by one. After 13 days, when 1 day remains until the scheduled dosing time, the display 161 is operated to show "01". The display 161 is operated to flash or blink to indicate that the scheduled dosing time is near. The display 161 is operated to flash by intermittently showing "01".

After 14 days, on the day of the scheduled dosing time, the display 161 is operated to show "00". The display 161 is operated to flash to indicate that the scheduled dosing time is due. The display 161 is operated to flash by intermittently showing "00". The flash periodicity of the display 161 may be of the order of 0.25 seconds to 2 seconds.

The processor arrangement 101 may check the state of charge of one or more batteries 170 included in the packaging assembly 100. If the state of charge is determined to be low, the display 161 may be operated to show a battery low warning.

The battery low warning shown by the display 161 may be a message comprising an upper case L on the first seven-segment array, and a lower case o on the second seven-segment array. That is, the display 161 may show the message "Lo". The battery low warning may be shown intermittently by the display 161 under the control of the processor arrangement 101.

The display 161 may be operated to show the battery low warning alternately with the number of days remaining until the scheduled dosing time. The periodicity of the intermittent or alternating operation of the display 161 may be of the order of 0.25 seconds to 2 seconds The electronics system 160 comprises the LED 162 of the user interface. The LED 162 can be operated to provide a notification. The LED 162 can be operated to provide an indication of a status of the packaging assembly 100. The LED 162 is an example of a status indicator.

The processor arrangement 101 can operate the LED 162 to provide a visual reminder that the scheduled dosing time is due. After 14 days, on the day of the scheduled dosing time, the LED 162 is operated to generate an intermittent output light. The LED 162 is operated to flash or blink in the colour red to provide a visual reminder that the scheduled dosing time is due. The flash periodicity of the LED 162 may be of the order of 0.25 seconds to 2 seconds.

The electronics system 160 comprises the speaker 163 of the user interface. The speaker 163 can be operated to output a notification signal. The speaker 162 can be operated to provide an indication of a status of the packaging assembly 100. The speaker 162 is an example of a status indicator.

The processor arrangement 101 operated the speaker 163 to provide an audio reminder that the scheduled dosing time is due. After 14 days, on the day of the scheduled dosing time, the speaker 163 is operated to output an audio reminder that the schedule dosage time is due. The speaker 163 may be operated to output an intermittent tone. The periodicity of the speaker 163 output may be of the order of 0.25 seconds to 2 seconds.

The processor arrangement 101 controls the operation of the speaker 163 according to the signal input by the lid open sensor 167. The processor arrangement 101 may control the operation of the speaker 163 according to the stored value of the lid flag. When the scheduled dosing time is due, the processor arrangement 101 operated the speaker 163 to output an audio indication that the scheduled dosing time is due, as described above. When the lid open sensor 167 provides a signal to the processor arrangement 101 to indicate that the lid 120 of the case 110 is open, the processor arrangement 101 controls the speaker 163 to deactivate the reminder.

When the lid open sensor 167 provides a signal to the processor arrangement 101 to indicate that the lid 120 is open, the processor arrangement 101 sets the lid flag to have a value of 1. The processor arrangement 101 controls the speaker 163 to deactivate the reminder when the stored value of the lid flag is equal to 1. The processor arrangement 101 resets the lid flag to have a value of 0 when the reset button 164 is pressed.

In this way, the audio reminder output by the speaker 163 is deactivated only when the lid opened by a user. The speaker 163 is deactivated only when the user opens the lid 120 of the case 110 in order to retrieve the injection device 10 for the scheduled dosage. The packaging assembly 100 thereby improves compliance with the scheduled dosage regime.

The processor arrangement 101 controls the display 161, the LED 162 and the speaker 163 according to an input from the fridge open sensor 166. If the fridge open sensor 166 indicated by signalling to the processor arrangement 101 that the fridge door is open, the processor arrangement 101 controls the display 161, the LED 162 and the speaker 163, as described above. If the fridge open sensor 166 does not indicate by signalling to the processor arrangement 101, the processor arrangement 101 does not activate the display 161, the LED 162 or the speaker 163.

In this way, the display 161, the LED 162 and the speaker 163 are not active when the fridge is closed. The user interface of the packaging assembly 100 is activated only when the fridge is open, therefore conserving the energy of the battery 170.

The processor arrangement 101 is configured to start the door timer from zero when the fridge door is opened. After the timer has been started, the device can be said to be in a door open state. The processor arrangement 101 is configured to enter a partial sleep state when the time period measured by the door timer is over 5 minutes. The display 161, LED 162 and the speaker 163 are turned off by the processor arrangement 101 in the partial sleep state.

Figure 5:
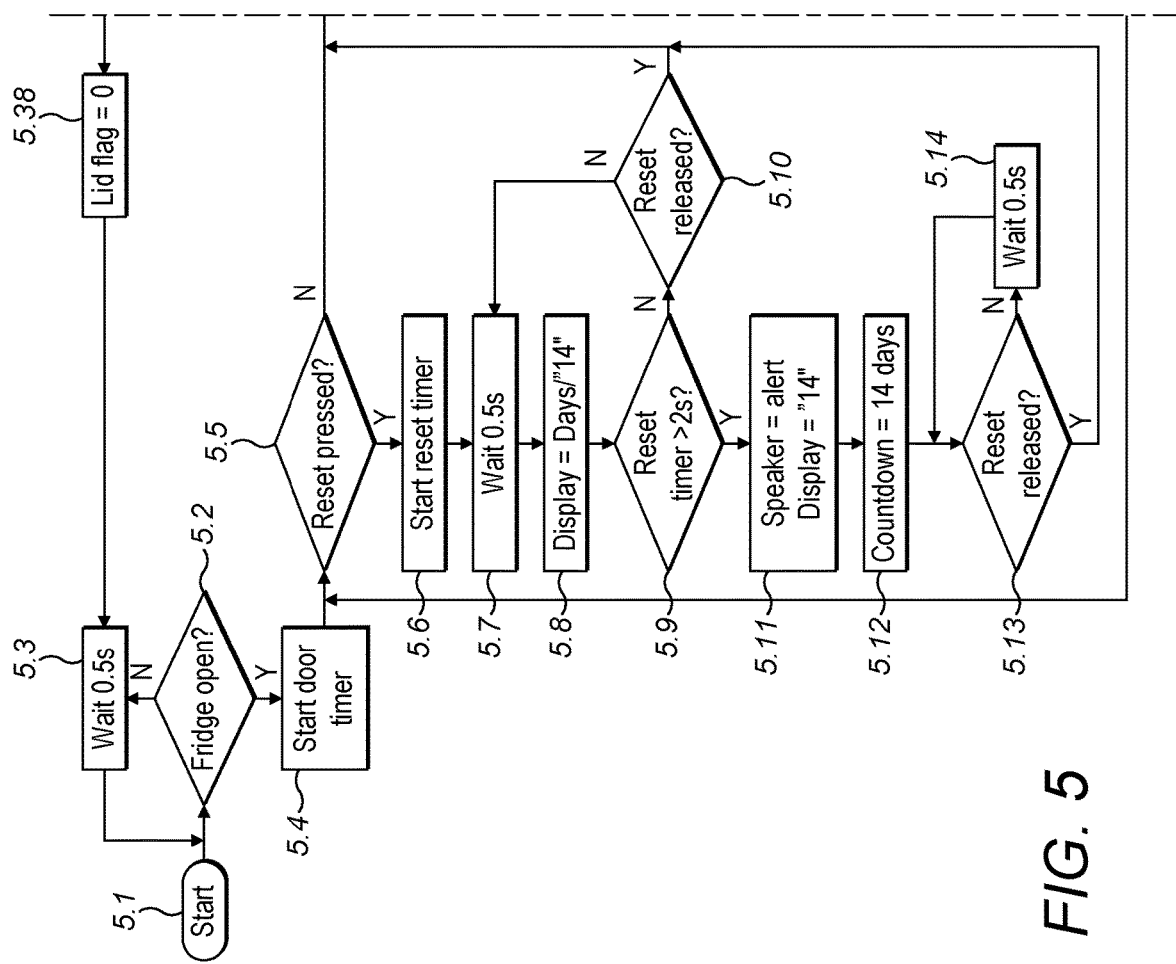
FIG. 5 is a flowchart illustrating a second exemplary operation of the packaging assembly, according to an exemplary embodiment.
Figure 5:
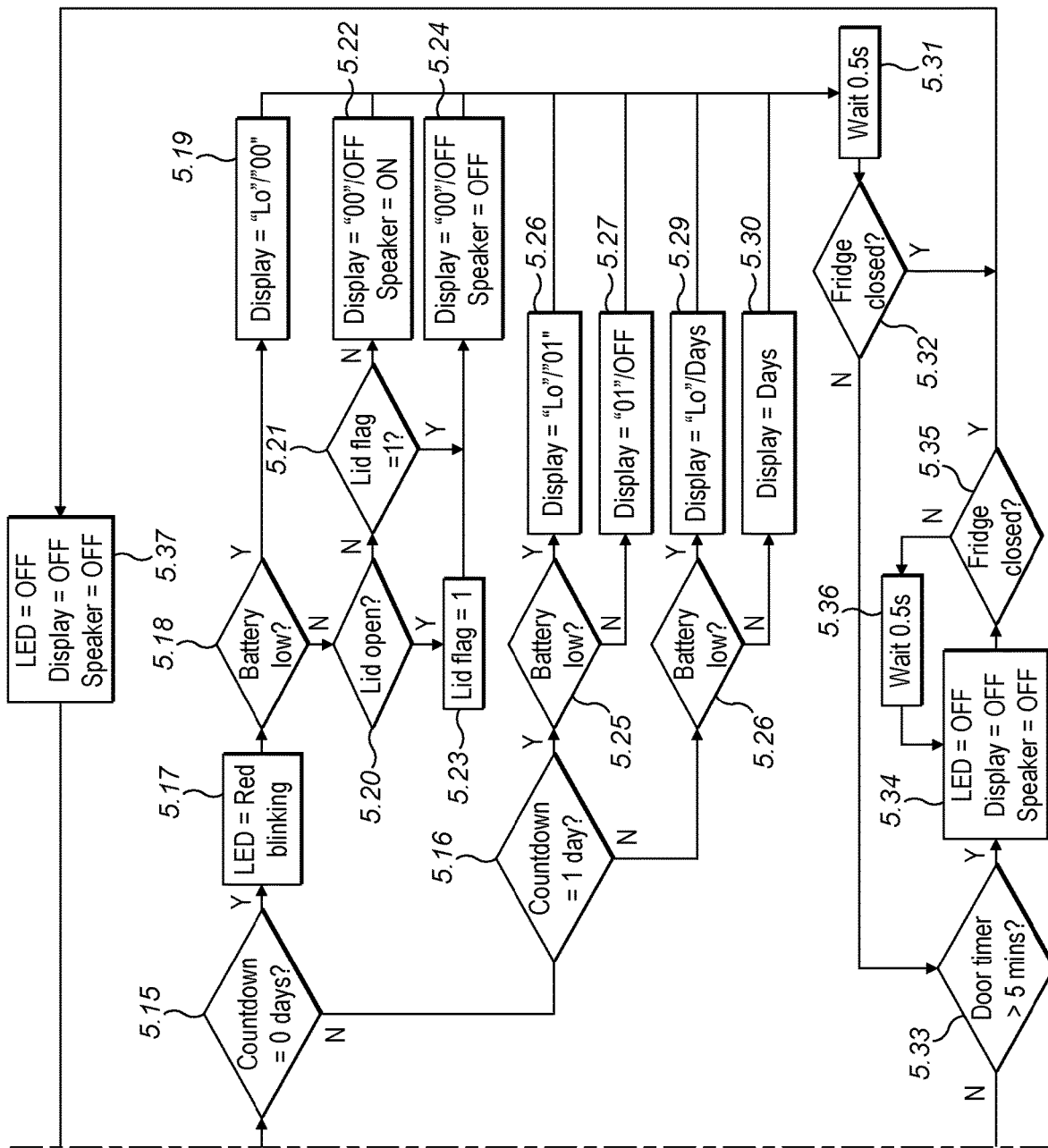

With respect to FIG. 5, a flowchart showing a second exemplary operation of the packaging assembly 100 is shown. The second exemplary operation of FIG. 5 supplements the first exemplary operation of FIG. 3. The second exemplary operation of FIG. 5 shows the first exemplary operation of FIG. 3 in a different manner, and includes more detail.

The process starts at step 5.1.

At step 5.2, the processor arrangement 101 checks whether or not the fridge door is open. The processor arrangement 101 checks whether a signal to indicate that fridge door is open is received from the fridge open sensor 166. If a signal is not received, the processor arrangement 101 proceeds to step 5.3. At step 5.3 the processor arrangement 101 waits 0.5 seconds before returning to step 5.2 and checking again whether or not the fridge is open. If a signal indicating that the fridge door is open is received by the processor arrangement 101, the processor arrangement 101 proceeds to step 5.4. At step 5.4, the processor arrangement 101 starts a timer to monitor for how long the fridge door has been open.

At step 5.5, the processor arrangement 101 checks whether or not the reset button 164 has been pressed. The processor arrangement 101 is configured to reset the countdown time to the scheduled dosing time only if the reset button 164 is held down for two seconds or more. If the processor arrangement 101 detects that the reset button 164 has been pressed, the processor arrangement 101 proceeds to step 5.6. At 5.6, the processor arrangement 101 starts a reset timer to monitor for how long the reset button 164 has been pressed.

After starting the timer, the processor arrangement 101 proceeds to step 5.7 and waits 0.5 seconds. At step 5.8, the processor arrangement 101 operates the display 161 to show alternately the current number of days and the number of days being set by the reset operation. In the usual case, the display 161 will show "00" and "14" alternately.

At step 5.9, the processor arrangement 101 checks whether or not the reset timer is over two seconds. If the reset timer is below two seconds, the processor arrangement 101 proceeds to step 5.10. At step 5.10, the processor arrangement 101 checks whether or not the reset timer button has been released.

If the reset button 164 is found to have been released before the reset timer has reached two seconds, then the processor arrangement 101 continues with the normal operation at step 5.15. If the reset button 164 has not been released, then the processor arrangement 101 returns to step 5.7 and waits 0.5 seconds before again checking the reset timer at step 5.9.

If the processor arrangement 101 finds that the reset timer is over two seconds, the processor arrangement 101 carries out a reset operation beginning with step 5.11. At step 5.11, the processor arrangement 101 operates the speaker 163 to output a short alert sound, to indicate to the user that the reset operation has been initiated. The processor arrangement 101 further operates the display to show "14". At step 5.12, the processor arrangement 101 sets the countdown for the schedule dosing time to be 14 days.

At step 5.13, the processor arrangement 101 checks whether or not the reset button 164 has been released. If the reset button 164 has been not been released, the processor arrangement 101 proceeds to step 5.14, and waits 0.5 seconds. The processor arrangement 101 then returns to step 5.13 and again checks whether or not the reset button 164 has been released. When the reset button 164 is determined to have been released, the processor arrangement 101 continues with the normal operation at step 5.15.

The processor arrangement 101 checks the countdown timer to the scheduled dosing time. First, at step 5.15, the processor arrangement 101 checks whether the countdown has reached zero days. If not, the processor arrangement 101 proceeds to step 5.16. At step 5.16, the processor arrangement 101 checks whether the countdown is at one day. If the countdown is not at zero days or one day, then the processor arrangement 101 determines that the countdown to the scheduled dosing time is greater than one day.

If the countdown to the schedule dosing time is zero days, then the processor arrangement 101 determines that the scheduled dosing time is due. At step 5.17, the processor arrangement 101 operates the LED 162 to blink.

At step 5.18, the processor arrangement 101 checks whether or not the battery 170 is low. If the battery 170 has a low state of charge, the processor arrangement 101 operates the user interface to indicate this to the user.

The state of charge is determined to be low if it is below a threshold. The threshold may be built into the design of the packaging arrangement. The state of charge may be determined by measurement of the voltage provided by the battery 170, by monitoring energy use from a full state of charge, or a combination of these two techniques.

At step 5.19, the processor arrangement 101 operates the display 161 to show a battery low warning message alternately with the number of days on the countdown.

The battery low warning shown by the display 161 comprises an upper case L on the first seven-segment array, and a lower case o on the second seven-segment array. That is, the display 161 shows the message "Lo". In this case, the number of days on countdown to the scheduled dosing time is zero days, so the display 161 shows alternately the message "Lo" and the number zero ("00").

If the number of days until the scheduled dosing time is due is zero days, and the state of charge of the battery 170 is determined not to be low, then the processor arrangement 101 controls the operation of the user interface according to whether or not the lid 120 is open. At step 5.20, the processor arrangement 101 determines whether or not the lid 120 is open by checking whether or not a signal is received from the lid open sensor 167 to indicate that the hinge switch 167 is pressed by the actuating part 128 of the lid 120. If the processor arrangement 101 determines that the lid 120 is not open, the processor arrangement 101 proceeds to step 5.21.

At step 5.21, the processor arrangement 101 checks whether or not the stored value of the lid flag is equal to 1. The lid flag indicates whether or not the lid 120 has been opened. If the lid has not been opened, the value of the lid flag is 0. When the lid flag is not equal to 1, the processor arrangement 101 determines that the lid 120 has not been opened. When the lid flag is not equal to 1, the processor arrangement proceeds to step 5.22. At step 5.22, the processor arrangement 101 operates the display 161 to flash the number of days, that is, zero days, and operates the speaker 163 to output a notification alert sound.

If the lid 120 is opened, the processor arrangement 101 determines at step 5.20 that the lid 120 is open. At step 5.23, the processor arrangement 101 sets a lid flag to have a value of 1. The lid flag indicates whether or not the lid 120 has been opened. At step 5.24, the processor arrangement 101 deactivates the speaker 163 and operates the display 161 to flash zero days.

In this way, a notification alert sound output by the speaker 163 can be deactivated only by the user opening the lid 120 to retrieve the required injection device 10. The packaging assembly 100 thereby improves compliance with the dosage regime.

If the lid 120 is closed, and the processor arrangement 101 determines at step 5.21 that the value of the lid flag is equal to 1, then the processor arrangement proceeds to step 5.24. At step 5.24, the processor arrangement 101 deactivates the speaker 163 and operates the display 161 to flash zero days. The speaker 163 remains deactivated if the lid 120 is closed again after being opened.

If the number of days until the scheduled dosing time is one day, the processor arrangement 101 turns off the LED 162. The processor arrangement 101 operates the display 161 according to state of charge of the battery 170. At step 5.25, the processor arrangement 101 checks whether or not the battery 170 is low. If the processor determines that the battery 170 is low, the processor arrangement 101 proceeds to step 5.26. At step 5.26, the processor arrangement 101 operates the display 161 to show the battery low warning message alternately with the number of days remaining on the countdown. In this case, the display 161 shows "Lo" alternately with "01". If the state of charge of the battery 170 is not low, the processor arrangement 101 proceeds to step 5.27. At step 5.27, the processor arrangement 101 operates the display 161 to flash the number of days on the countdown. In this case, the display 161 flashes "01".

If the number of days until scheduled dosing time is greater than one day, the processor arrangement 101 controls the LED 162 to be off. The processor arrangement 101 operates the display 161 according to the state of charge of the battery 170. At step 5.28, the processor arrangement 101 checks whether or not the battery 170 is low. If the processor arrangement 101 determines that the battery 170 is low, then the processor arrangement 101 proceeds to step 5.29. At step 5.29, the processor arrangement 101 operates the display 161 to show the battery low warning message alternately with the number of days remaining until the schedule dosing time. If the state of charge of the battery 170 is not low, then the processor arrangement 101 proceeds to step 5.30. At step 5.30, the processor arrangement 101 operates the display 161 to show the number of days remaining.

The processor arrangement 101 thereby controls the output of the user interface according to the number of days remaining until the scheduled dosing time, according to the state of charge of the battery 170, and according to whether or not the lid 120 of the case 110 is open. After setting the output of the user interface, the processor arrangement 101 proceeds to step 5.31 and waits 0.5 seconds.

At step 5.32 the processor arrangement 101 checks whether or not the fridge door is closed. The processor arrangement 101 checks whether the signal to indicate that the fridge door is open is still being received from the fridge open sensor 166. If the processor arrangement 101 determines the fridge door is open, the processor arrangement 101 proceeds to step 5.33.

At step 5.33, the processor arrangement 101 checks the time currently on the door timer. The processor arrangement 101 checks whether or not the door timer is over five minutes. That is, the processor arrangement 101 checks whether the door of fridge has been open for more than five minutes. If the door of the fridge has been open for a period of less than five minutes, then the processor arrangement 101 returns to an earlier point of operation at step 5.5, immediately after the initial point of starting the door timer. The processor arrangement 101 again checks the reset button 164, checks the countdown until the scheduled dosing time, checks the state of charge of the battery 170, and checks the state of the lid 120 before setting the output of the user interface.

If the processor arrangement 101 determines that the door of the fridge has been open for a period longer than five minutes, the processor arrangement 101 controls the user interface to enter a partial sleep state. At step 5.34, the processor arrangement 101 turns off the LED 162, the speaker 163, and the display 161, in order to conserve power. At step 5.36, the processor arrangement 101 checks again whether or not the fridge door has been closed. If the processor arrangement 101 determines that the fridge door is open, the processor arrangement 101 proceeds to step 5.36 and waits 0.5 seconds before returning to step 5.34.

If the processor arrangement 101 determines at step 5.35 that the fridge door has been closed, the processor arrangement 101 proceeds to step 5.37. At step 5.37, the processor arrangement 101 turns off the LED 162, the display 161 and the speaker 163. At step 5.38, the processor arrangement 101 sets the lid flag to have a value of 0, before returning to step 5.3, At step 5.3, the processor arrangement 101 waits 0.5 seconds before checking whether or not the fridge door has been opened, as described above.

This provides a door open timer that is activated in response to a determination of an intensity of light sensed by the light sensor rising above the threshold amount of light. The door open timer is cancelled in response to a determination of the intensity of light sensed by the light sensor falling below the threshold amount of light, which corresponds to the door being closed. If the time expires before it is cancelled, it is determined that the fridge door has been left open unintentionally and optical and audio alerts and visual indications of remaining time to day zero are suppressed. This reduces power consumption of the device with relatively little reduction in useful alerting. Once the fridge door is shut again, normal operation resumes. When subsequently the fridge door is again opened, alerting and indication occurs as usual in the door open mode.

Figure 6:
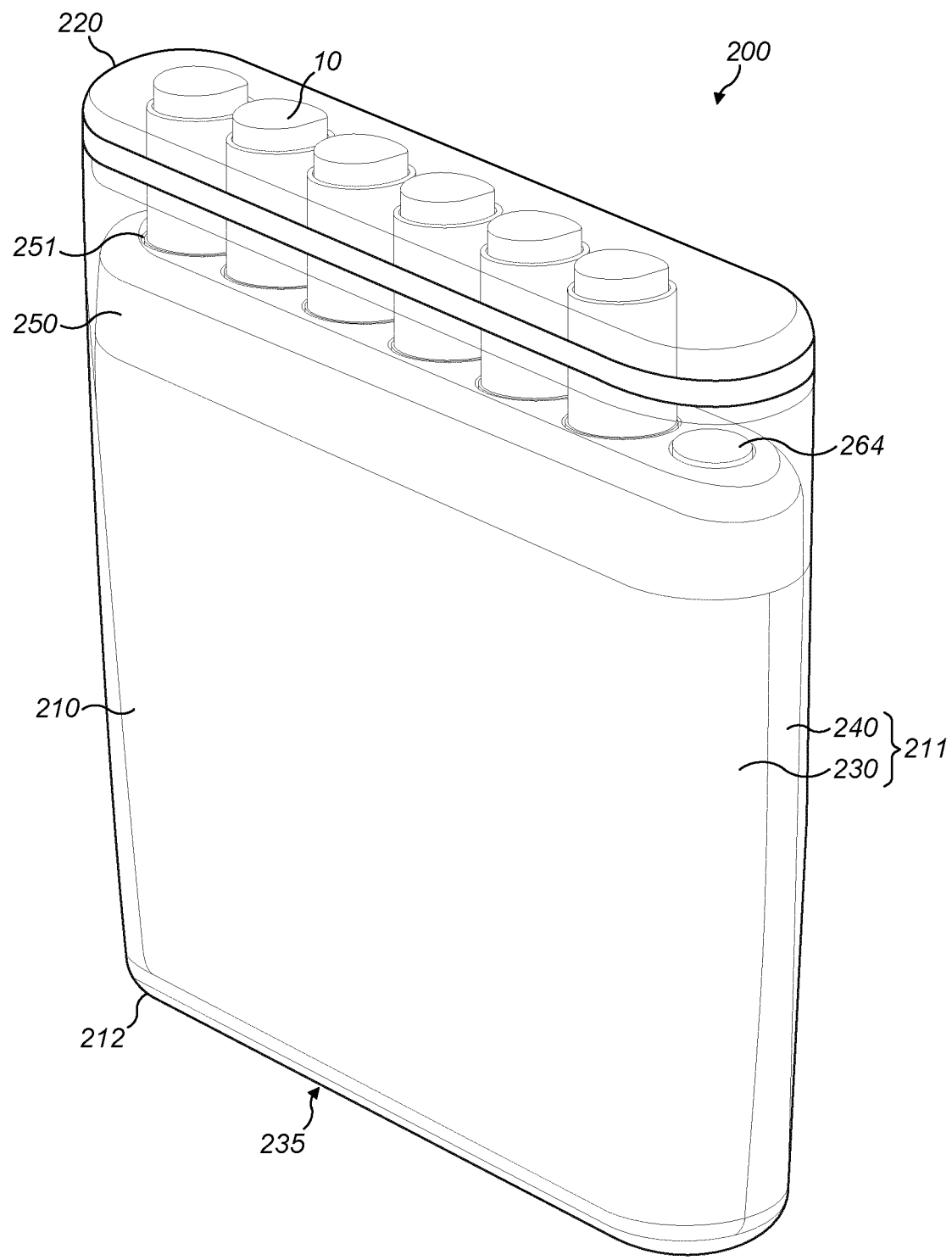
FIG. 6 is an isometric view of a packaging assembly according to an exemplary embodiment.

With respect to FIG. 6, a packaging assembly 200 according to a second embodiment is shown. Elements not described below are substantially the same as those of the first embodiment.

A case 210 is formed having rounded side walls. The case 210 is formed from a first part 230 and a second part 240. The vertically extending side edges of the first part 230 are curved to meet the second part 240. The vertically extending side edges of the second part 240 are curved to meet the first part 230. The first part 230 and second part 240 form a flat base 235 of the case 210.

The case further comprises an upper part 250. The upper part 250 is configured to engage with a top edge of the first part 230 and a top edge of the second part 240. The upper part 250 holds the first part 230 and the second part 240 of the case 210 together. A plurality of openings 251 are formed in a top face of the upper part 250 to receive a plurality of injection devices 10.

The first part 230 and the second part 240 form an inner housing 211. The case 210 further comprises an outer housing 212. The outer housing 212 encases the first part 230 and the second part 240. The outer housing 212 is transparent. Alternatively, at least a portion of the outer housing may be translucent or may be opaque.

An upper portion of the outer housing 212 extends upwards from the inner housing 211. The outer housing 212 surrounds the upper part 250 of the case 210. The outer housing 212 is formed to extend beyond the top ends of injection devices 10 which are located in the openings 251. A top edge of the outer housing 212 forms an opening at the top of the case 210.

The packaging assembly 200 comprises a lid 220. The lid 220 is configured to removably cover the opening formed in the outer housing 212. In a closed position the lid 220 is placed over the opening at the top of the case 210. A friction fit is formed between the lid 220 and the outer housing 212 in the closed position. In an open position the lid 220 is removed from the opening and is not connected to the case 210. Alternatively, the lid 220 may be connected to the outer housing 212 using a hinge.

A user interface of the packaging assembly 200 comprises a reset button 264. The reset button 264 is formed from a translucent plastic material. The reset button 264 comprises an LED (not shown) located within the reset button 264. The LED is configured to illuminate the translucent material of the reset button 264 when activated. The translucent material diffuses the light emitted by the LED so as to illuminate the entire reset button 264.

The reset button 264 and LED may be controlled as described with respect to the reset button 164 and notification LED 163 of the first embodiment.

Alternatively, the LED may be turned on without flashing when the number of days on the countdown is greater than zero, and controlled to flash when the number of days is equal to zero. The reset button 264 is illuminated to indicate that the status of the packaging assembly 200 is normal, and flashes to indicate that the scheduled dosing time is due.

Figure 7:
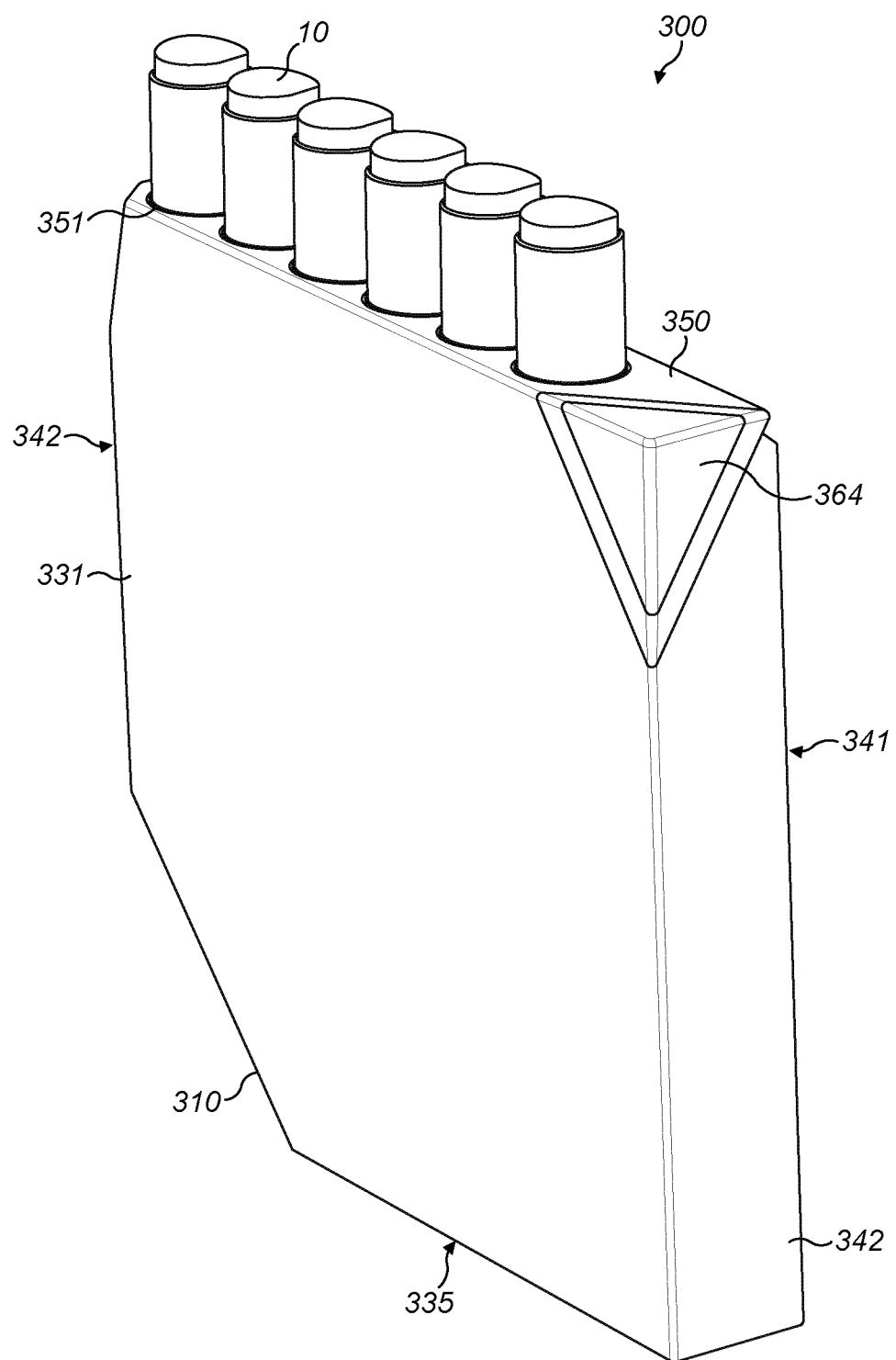
FIG. 7 is an isometric view of a packaging assembly according to an exemplary embodiment.

With respect to FIG. 7, a packaging assembly 300 according to a third embodiment is shown. Elements not described below are substantially the same as those of the first embodiment.

The packaging assembly 300 comprises a case 310. The case 310 is provided without a lid. The case 310 is generally rectangular, having a front face 331, a rear face 341, a base 335 and two side walls 342. A top panel 350 of the case 310 comprises a plurality of openings 351 to receive a corresponding plurality of injection devices 10. The packaging assembly 300 may include a retention mechanism to hold the injectors in position in the openings 351.

The case 310 further comprises a reset button 364. The case 310 is formed having a top corner cut away to form a flat angled surface. The reset button 364 is located on the angled surface. The reset button 364 is a triangular pyramid shape. The reset button 264 is shaped so as to complete the rectangular corner of the case 310.

The reset button 364 is formed from a flexible plastic or rubber material. The flexible reset button 364 may be depressed by a user in order to actuate a reset switch (not shown) positioned beneath. The reset button 364 is formed from a translucent material.

The reset button 364 comprises an LED (not shown) located within the reset button 364. The LED is configured to illuminate the translucent material of the reset button 364 when activated. The translucent material diffuses the light emitted by the LED so as to illuminate the entire reset button 364.

The reset button 364 and LED may be controlled as described with respect to the reset button 164 and notification LED 163 of the first embodiment or the reset button 264 and LED of the second embodiment.

Figure 8:
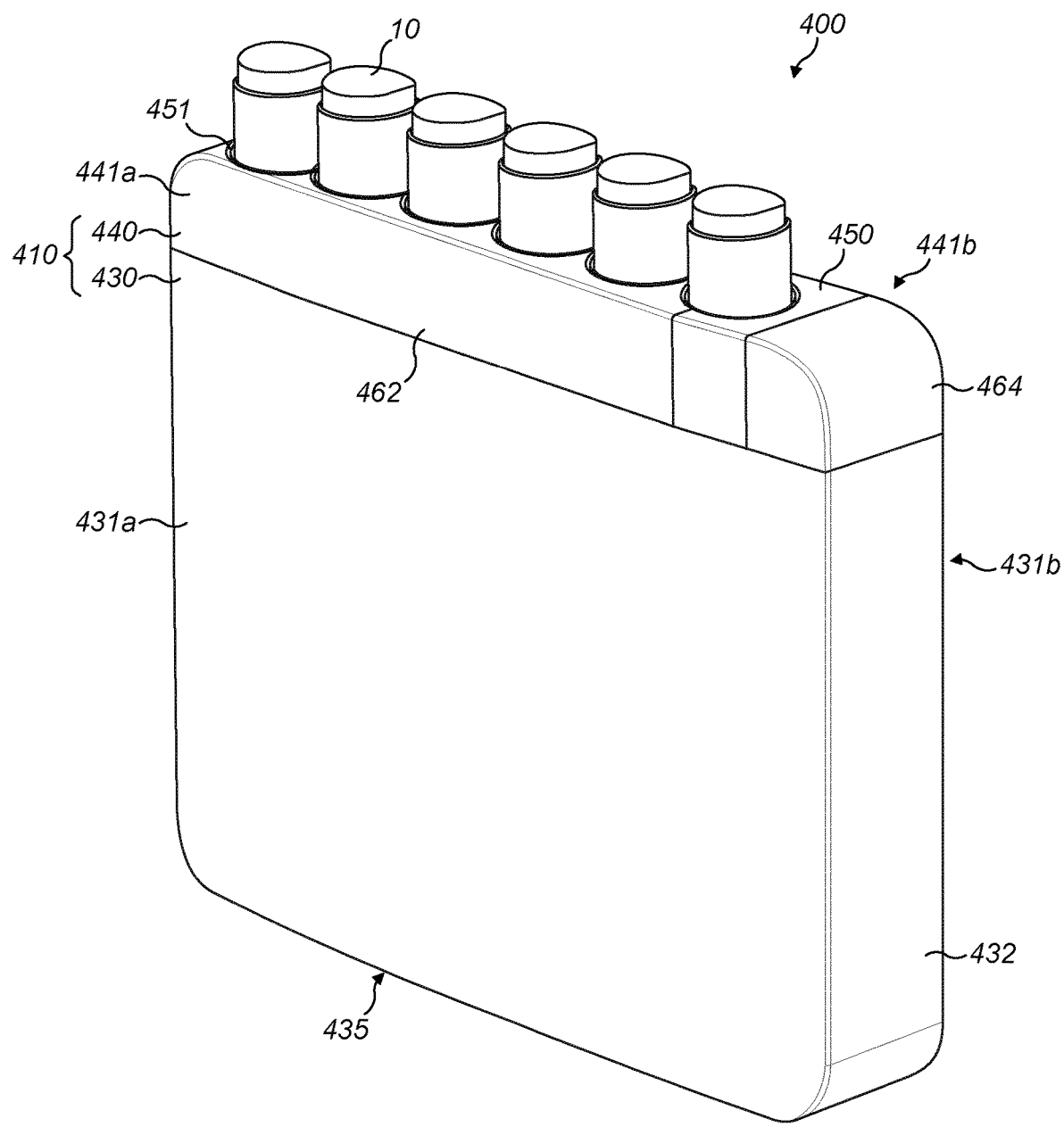
FIG. 8 is an isometric view of a packaging assembly according to an exemplary embodiment.

With respect to FIG. 8, a packaging assembly 400 according to a fourth embodiment is shown.

Elements not described below are substantially the same as those of the first embodiment.

The packaging assembly 400 comprises a case 410. The case 410 is provided without a lid. The case 410 is generally rectangular. The case 410 comprises having a first lower part 430 and a second upper part 440.

The first part 430 of the case 410 comprises a front face 431a, a rear face 431b, a base 435 and two side walls 432. The first part 430 is formed from an opaque plastic material. The lower corners of the front face 431a and the rear face 431b are rounded. The two side walls 432 have a corresponding curvature at their respective lower ends to meet the base 435 of the case 410.

The front face 431a, the rear face 431b and the two side walls 432 are coupled to the second part 440 at the upper end of the first part 430.

The second part 440 of the case 410 extends upwards from first part 430. The second part 440 comprises a front face 441a, a rear face 441b and a top panel 450. The upper corners of the front face 441a and the rear face 441b are rounded. The top panel 450 has a corresponding curvature at each end to meet the two side walls 432 of the first part 430 of the case 410. The front face 441a and the rear face 441b are coupled to the first part 430 at the lower end of the second part 440.

The second part 440 of the case 410 is formed from a translucent material. The top panel 450 comprises a plurality of openings 451 to receive a plurality of injection devices 10. The packaging assembly 400 may include a retention mechanism to hold the injectors in position in the openings 451.

A portion of the second part 440 forms a reset button 464. The portion forming the reset button 464 comprises the curved portion at one end of the top panel 450 and the adjacent portions of the front face 441a and the rear face 441b. The reset button 464 is formed from a flexible plastic or rubber material. The reset button 464 may be formed from an opaque material. The flexible reset button 464 can be depressed by a user in order to actuate a reset switch (not shown) positioned beneath.

The packaging assembly 400 comprises an LED 462. The LED 462 is arranged within the translucent portion of the second part 440. Light emitted by the LED 462 is diffused by the translucent material of the case 410 and illuminates the entire portion of the second part 440 between the plurality of openings 451.

The reset button 464 and LED 463 may be controlled as described with respect to the reset button 164 and notification LED 163 of the first embodiment or the reset button 264 and LED of the second embodiment.

Alternatively, the packaging assembly 400 may comprise a plurality of LEDs. The plurality of LEDs may be provided corresponding to the plurality of openings. When the scheduled dosing time is due, the processor arrangement may control the plurality of LEDs in combination to provide a visual reminder alert. The plurality of LEDs may be controlled to flash in unison.

Figure 9:
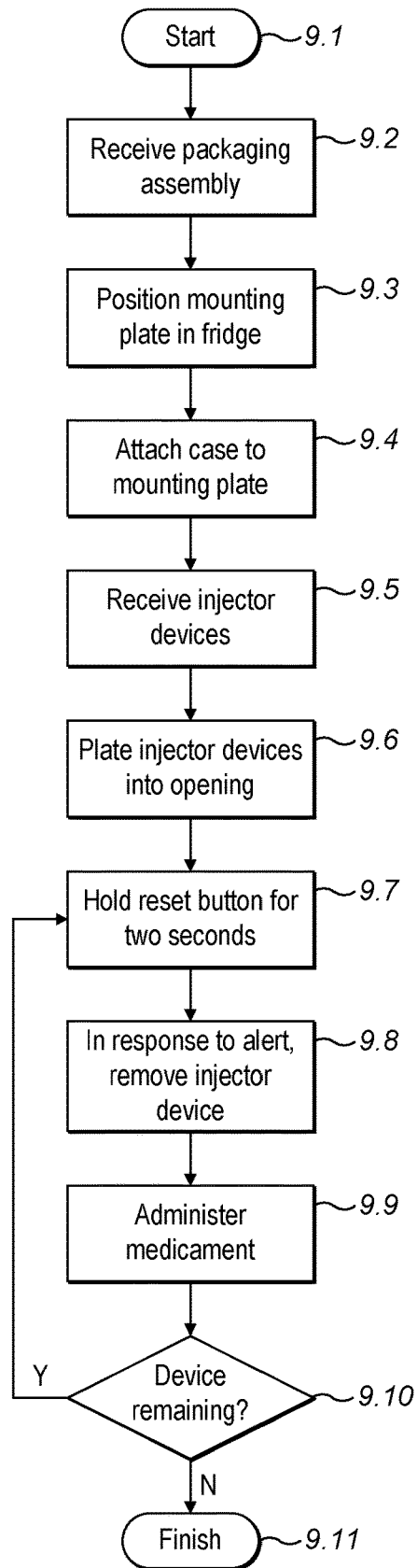
FIG. 9 is a flowchart illustrating an exemplary user operation of the packaging assembly according to any embodiment.

A first exemplary user operation of the packaging assembly 100 will now be described with respect to FIG. 9.

The operation starts at step 9.1.

At step 9.2, the user receives the packaging assembly 100. The packaging assembly 100 may be empty. The packaging assembly 100 may include one or more batteries 170. Alternatively, the user may insert batteries 170 into the battery opening 145.

The user then places the packaging assembly 100 into a refrigerator or fridge. At step 9.3, the mounting plate 180 is fixed to an internal surface of the fridge using the adhesive strips 191. At step 9.4, the case 110 of the packaging assembly 100 is attached to the mounting plate 190 by magnets 148. The empty packaging assembly 100 may be placed in the fridge until an internal temperature of the case 10 has cooled to reach the temperature of the fridge.

At step 9.4, the user receives a plurality of injection devices 10. The user may receive six injection devices 10, in order to provide a medicament dosage every 14 days over the course of about 3 months. Alternatively, the six injection devices 10 may be administered every 28 days over the course of about 6 months.

At step 9.5, the user places the injection devices 10 into the openings 151 of the case 110.

At step 9.6, the user holds the reset button for at least 2 seconds. The countdown timer of the processor arrangement 101 is reset. The time period to the scheduled dosing time is set to be 14 days. The user can now use the fridge as normal until the scheduled dosing time is due.

After 14 days, when the scheduled dosing time is due, the user is provided with a reminder alert upon opening the fridge. The user may be provided with a visual reminder alert. The user may be provided with an audio reminder alert.

At step 9.7, in response to the reminder alert, the user removes an injection device 10 from the case 110. The audio reminder alert is deactivated when the lid 120 of the packaging assembly 100 is opened.

At step 9.8, the user administers the medicament using the injection device 10.

At step 9.9, the user checks the number of injection devices 10 remaining in the packaging assembly 100. If there is at least one injection device 10 in the packaging assembly 100, the user returns to step 9.6 and holds the reset button for at least 2 seconds.

If there are no injection devices 10 remaining in the packaging assembly 100, the operation finishes at step 9.10.

Figure 10:
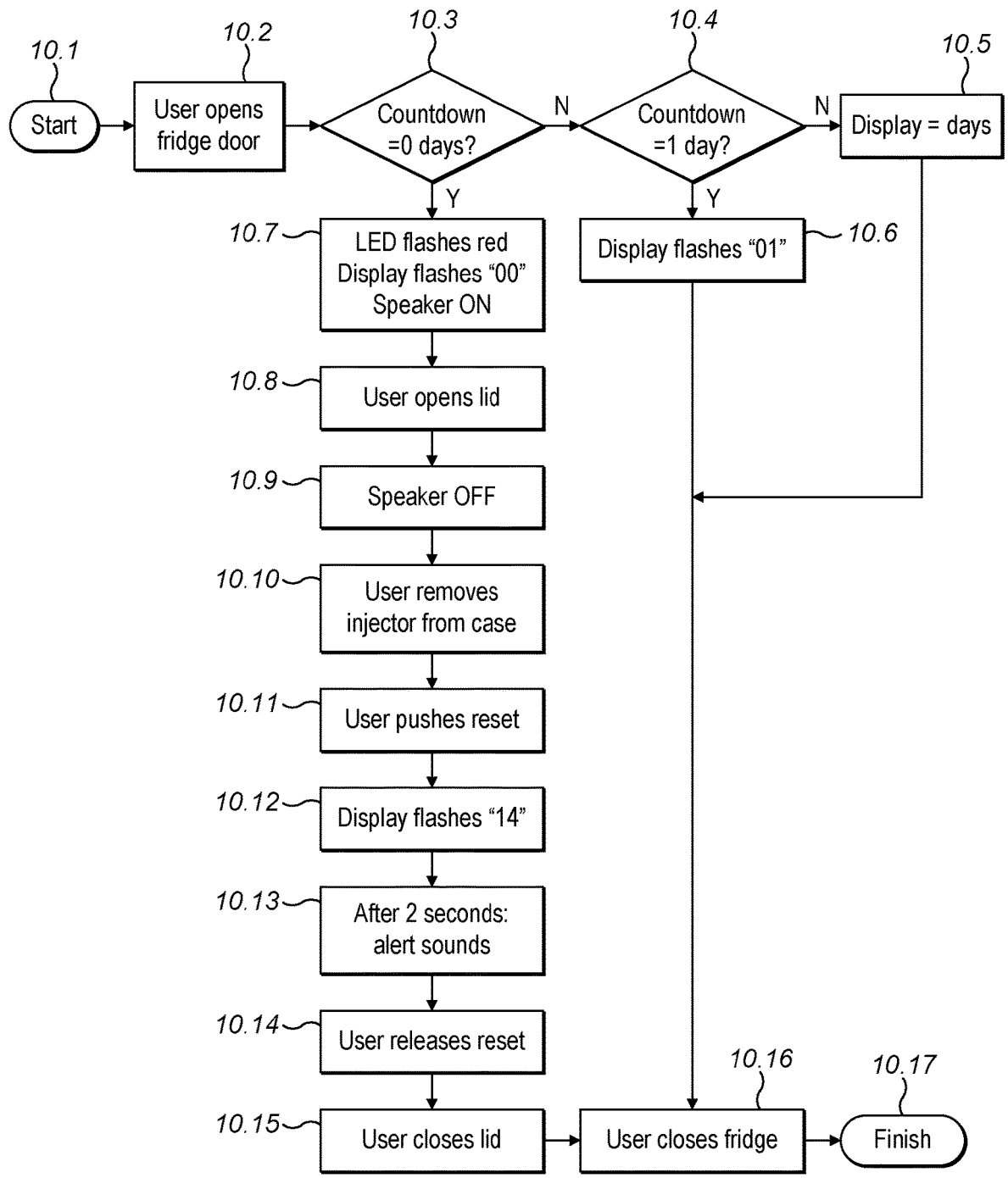
FIG. 10 is a flowchart illustrating an exemplary user operation of the packaging assembly according to any embodiment.

With respect to FIG. 10, a flowchart showing a second exemplary user operation of the packaging assembly 100 is shown. The second exemplary user operation of FIG. 10 supplements the first exemplary user operation of FIG. 9. The second exemplary user operation of FIG. 10 shows the first exemplary user operation of FIG. 9 in a different manner, and includes more detail.

The operation starts at step 10.1.

At step 10.2, the user opens the fridge door. The user may open the fridge door specifically to check the packaging assembly 100, or as part of their daily routine. The user may be taking food from the fridge or placing food into the fridge.

If the number of days remaining until the scheduled dosing time is greater than 1 day, then the countdown timer is not equal to 0 days at step 10.3 and the operation proceeds to step 10.4, The countdown timer is not equal to 1 day and the operation proceeds further to step 10.5.

At step 10.5, the display 161 shows the number of days remaining until the scheduled dosing time. The user can see the static blue light of the display through the translucent lid 120. The user can read the display through the viewing window 121. The number of days is shown until the user closes the fridge door at step 10.16. For the purpose of this illustration, it is assumed that the user closes the fridge door within 5 minutes of it being opened, so alert suppression is not provided.

If the number of days remaining until the scheduled dosing time is 1 day, then the countdown timer is determined to be equal to 1 day at step 10.4, and the operation proceeds to step 10.6.

At step 10.6, the display 161 flashes the number of days remaining until the scheduled dosing time. That is, the display 161 flashes "01". The user can see the flashing blue light of the display 161 through the translucent lid 120. The user can read the display 161 through the viewing window 121. The number "01" is flashed until the user closes the fridge at step 10.16.

If the number of days remaining until the scheduled dosing time is 0 days, then the countdown timer is equal to 0 days at step 10.3, and the operation proceeds to step 10.7.

At step 10.7, the display 161 flashes the number "00", the LED 162 flashes red and the speaker 163 outputs an intermittent tone, The user can see the flashing blue light of the display 161 and the flashing red light of the LED through the translucent lid 120. The user can read the display 161 through the viewing window 121. The user can hear the intermittent tone output by the speaker 163.

At step 10.8, the user opens the lid 120 of the packaging assembly 100.

At step 10.9, the speaker 163 is turned off. The speaker 163 is turned off in response to the lid 120 being moved from a closed position to an open position.

At step 10.10, the user removes an injection device 10 from the case 110.

At step 10.11, the user pushes the reset button 164. The user holds down the reset button 164.

At step 10.12, the display 161 flashes the number "14". The display flashes in response to the reset button 164 being pushed, The display flashes "14" alternately with the current number of days until the scheduled dosing time, that is, the display flashes "14" and "00".

At step 10.13, after the reset button 164 has been held for 2 seconds, the speaker 163 outputs an alert sound.

At step 10.14, the user releases the reset button 164. The countdown time until the scheduled dosing time is reset to 14 days.

At step 10.15, the user closes the lid 120.
At step 10.16, the user closes the fridge door.
The operation finishes at step 10.17.

Figure 11A:
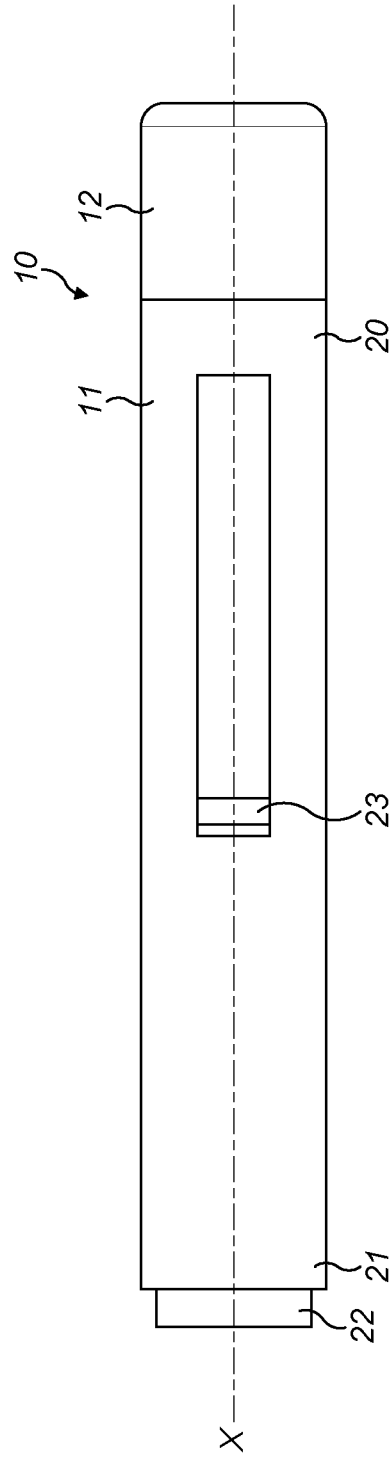
FIGS. 11A and 11B are side-on views of an auto-injection device for use with the packaging assembly, according to an exemplary embodiment.
Figure 11B:
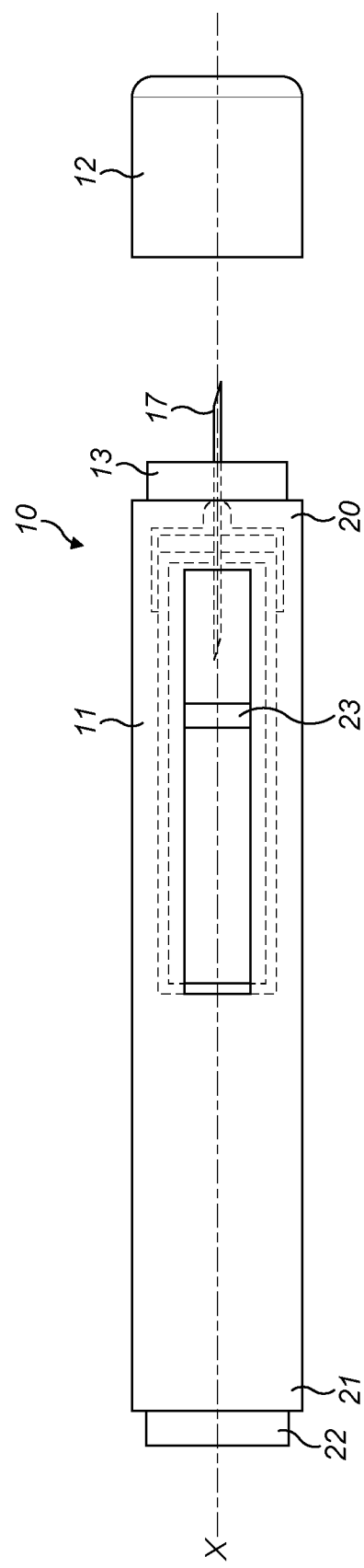

With respect to FIGS. 11A and 11B, an exemplary injection device 10 is shown. Injection device 10, as described above, is configured to inject a medicament into a user's body. Injection device 10 includes a housing 11 which typically contains a reservoir containing the medicament to be injected (e.g., a syringe) and the components required to facilitate one or more steps of the delivery process. Injection device 10 can also include a cap assembly 12 that can be detachably mounted to the housing 11. Typically a user must remove cap 12 from housing 11 before injection device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Injection device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a user's body and moving housing 11 in a distal direction will uncover the distal end of needle 17. Such relative movement allows the distal end of needle 17 to extend into the user's body. Such insertion is termed "manual" insertion as needle 17 is manually inserted via the user's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a user's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

It will be appreciated that the above described embodiments are purely illustrative and are not limiting on the scope of the claims. Other variations and modifications will be apparent to persons skilled in the art upon reading the present application, and some will now be described.

The case of the packaging arrangement may be a generally rectangular shape or may be any other shape suitable for containing the plurality of injectors. The case may be a suitable shape and size for placement within a household refrigerator.

The case may be formed to enclose the injectors and may be sealed, Alternatively, the case may be formed as a structure for supporting the plurality of injection devices externally. The injectors may be arranged in one or more rows, e.g. a row of six or two rows of three, or in a circular arrangement. The injectors may be arranged to hang below a supporting structure.

The case may be configured to store any number of injection devices, according to the dosage requirements of the medicament. For example, the case may store between 5 and 15 injection devices. Case may be sized to store enough injection devices for one quarter, or for a 6 month period. Where medicament is administered more regularly, the case may store enough injectors for one week.

The case may be formed of an opaque material. One or more of the components of the case may be formed with at least a transparent portion. A transparent portion of the case may allow the user to see the number of injection devices, or to see the user interface. One or more components of the case may be translucent to improve visibility of a visual reminder output.

The case may be formed of a plastics material such as polyethylene, polystyrene, polycarbonate, or it may be made of any other suitable material. Desired properties for the material of the case include temperature stability, moderate impact strength, resistance to cleaning fluids, a wipe-clean finish, and rigidity.

Each part of the case may be formed in a single piece e.g. a moulded plastic part. Alternatively, parts may be machined. The body of the case may be formed from two parts joined or attached together, or may be formed in a single part. An internal of the case may be formed as a single large cavity, a cavity divided into a plurality of areas for holding each injector, or may be formed as a plurality of cavities for individually holding each injector.

The case may comprise any number of magnets sufficient to support the weight of the packaging arrangement and injection devices. For example, the case may include 2 larger magnets or an arrangement of 6 smaller magnets. The magnets may be any permanent magnets and may be rare earth magnets. The magnets may be formed of neodymium or may be formed of samarium cobalt.

The case may further comprise one or more ventilating apertures to allow air flow into the case. Alternatively, the case may be sealed when the lid is in a closed position. The lid may further comprise a rubber seal to prevent air passing into the case between the lid and the case. The case may be insulated to maintain the low temperature of the injectors if removed from the fridge for a short period of time.

The lid may be coupled to the case with a hinge. The mechanism for connecting the lid to the case and for allowing the lid to open and close may take any suitable form. Instead of the hinge mechanism described above, the hinge may be a butt hinge, a living hinge or some other type. The lid may be coupled to the case with a flexible and/or elastic material. The hinge may allow some translational movement as well as pure rotational movement, to allow better viewing of or access to the internal part of the case when the lid is open.

The hinge may allow the removal of the lid by a user. For instance, the protrusions of each of the second hinging parts may be pushed inwards to disengage from the respective first hinging parts and decouple the lid from the case. The user may be provided with one or more alternative lids which may be a different design, for example, a different colour. An alternative lid may have a larger transparent portion or may be entirely opaque.

Alternatively, the lid may slidably engage with the case. The lid may comprise runners at the edges, each configured to engage with a corresponding groove on the case. The lid may slide out of the grooves and decouple from the case. The lid may be arranged to slide to the limit of the grooves and pivot freely in the open position. Further alternatively, the lid may be separate from the case and fixedly attached thereto with a friction fit. The lid may fit tightly within the opening at the upper end of the case, or may fit over an upper portion of the case.

The lid may comprise a latch to maintain the lid in the closed position. The latch may comprise a sliding catch arranged to slidably move between a first position and a second position. The catch may be arranged to protrude from an edge of the lid in the first position. The catch may be configured to slidably retract to not protrude in the second position. The latch may comprise a spring to urge the catch to the first position. The catch may be configured to engage with an opening in the case in the first position when the lid is in the closed position. The catch may engage with the opening to maintain the lid in the closed position.

The latch may be a sprung push-catch push-release mechanism. The latch may be configured to engage with a first push into the closed position and maintain the lid in the closed position. The latch may be configured to disengage with a second push and allow the lid to open. The latch may be configured to engage when the lid is closed to hold the lid in the closed position. The latch may further comprise a release switch to disengage the latch and allow the lid to open. The release switch may be a mechanical switch or an electric switch. The release switch may be an electric switch coupled to a code input, which is configured to disengage the lid catch when a correct code is entered.

Although the lid open sensor is described as an electromechanical switch, it may instead be an optical sensor arrangement, a magnetic sensor arrangement or any other suitable arrangement that is configured to detect whether the lid is open or closed or whether the lid is transitioning from a closed position to an open position.

The packaging assembly may comprise a case without a lid. The packaging assembly may not include a lid open sensor. The speaker may instead be deactivated by the processor arrangement according to an alert timer. The processor arrangement may be configured to operate the alert timer. The processor arrangement may activate the alert timer when the speaker is controlled to output an audio reminder alert that the scheduled dosing time is due. The processor arrangement may activate the alert timer when the scheduled dosing time is due, conditional on the fridge door being open. The processor arrangement may deactivate the speaker when the alert timer reaches 30 seconds. Alternatively, the processor arrangement may activate the alert timer at 20 seconds and count down until the timer expires. The processor arrangement may be configured to deactivate the speaker when the alert timer expires. The expiry time period for the alert timer may be 5 seconds to 60 seconds.

The electronics system may include an injector sensor to determine whether an injector is positioned in one of the plurality of openings. The injector sensor may determine whether an injector is positioned within each of the openings. The processor arrangement may be configured to deactivate the speaker when the injector sensor indicates that an injector has been removed from an opening.

The injector sensor may comprise one or more injector switches. The injector switches may be arranged respectively within the openings. Each injector switch may be a mechanical switch. The injector switch may be an normally open switch which is pressed to a closed position by an injector pen when in position in the opening. The injector switch may be a membrane switch. The injector switch may be actuated by a lever located within the opening.

Each injector switch may be configured to send a signal to the processor arrangement when a injector is located within the corresponding opening. The processor arrangement may be configured to deactivate the speaker when a signal is no longer received from an injector switch. The processor arrangement may be configured further to reset the countdown to the scheduled dosing time when an injector is removed from the opening. Alternatively, where an injector is replaced in the case after the dose is administered, the processor arrangement may be configured to reset the countdown when the injector is replaced. The processor arrangement may be configured to monitor the number of injectors in position in the packaging assembly. The processor arrangement may control the display to show the number of injectors in the packaging assembly. The processor arrangement may control the electronics system to provide a notification output when the packaging assembly is empty.

The retention mechanism may be arranged at the lower end of the case. The retention mechanism may be arranged to engage with the end of each injector which is passed through the opening. The retention mechanism may comprise a further plurality of openings at the lower end of the case. The further openings may be sized so as to hold the injectors in position with a friction fit. Alternatively, the retention mechanism may comprise a levered pincer arrangement arranged to grip the sides of an injector when the injector is pushed longitudinally into the arrangement, and to release the injector when the injector is pulled longitudinally out of the arrangement.

The retention mechanism may comprise a release switch configured to disengage the retention mechanism. The release switch may be configured to release one or all of the injectors. A plurality of release switches may be provided for the corresponding plurality of injectors. The release switch may be a mechanical switch or lever coupled to the retention mechanism. The release switch may be further coupled to an ejection mechanism. The release switch may be an electromechanical switch. The release switch may be controlled by the processor arrangement. The processor arrangement may control the release switch to disengage the retention mechanism conditional on the scheduled dosing time being due. The processor arrangement may control the release switch to disengage the retention mechanism for one injector when the scheduled dosing time is due.

The ejection mechanism may comprise one or more springs arranged to push a portion of the respective injectors out of the corresponding openings. The ejection mechanism may be biased against the retention mechanism to push each injector when released by the retention mechanism. The retention mechanism may be controlled to release one injector, which is pushed partially out of the opening by the ejection mechanism. This arrangement may provide a visual reminder alert in the form of a portion of the injector being pushed out of the opening.

Alternatively, the ejection mechanism may comprise a motorised actuator. For example, a roller arranged perpendicularly to the plurality of injectors may be driven to push the injectors out of the openings. The roller may push all of the injector equally, with the retention mechanism configured to hold all but one of the injectors in position. Further alternatively, the actuator may comprise a protruding part from the base of the case which is driven laterally across the width of the case. The protruding part may be driven along a rail, or may protrude from a belt extending along the width of the case. The protruding part is configured to engage with each injector in turn and push the injector out of the opening.

The time period for a reminder may be any suitable dosing period, dependent upon the medicament which is stored in the packaging assembly. The time period set until the next scheduled dosing time may be any number of days and may be, for example, between 2 and 60 days. The time period may be a number of weeks, for example, a period of 7 days, 14 days, 21 days or 28 days. The time period may be 28 days, which is 4 weeks, or the time period may be 1 month.

Alternatively, the time period may be 1 or 2 days, and the display may be configured to show the number of hours until the scheduled dosing time is due. Similarly, for a time period on the order of a number of hours, the display may show a number of minutes.

The timer duration switch may be configured to select between any two time periods. For example, the first switch position may correspond to a time period of 7 days and the second switch position may correspond to a time period of 14 days. Alternatively, the timer duration switch may be a multi-positional switch, for example, a rotary switch or a dial. The time period may be set in conjunction with the display, wherein a first user input causes the display to show the current time period, and a second input is used to adjust the time period.

The door timer and reset timer may operate on any suitable timeframe. For example, the user interface may enter the partial sleep mode if the fridge door is open for 10 minutes or 15 minutes. The reset button may be configured to reset the countdown timer if pressed for 1 second or up to 5 seconds.

The display may comprise more than 2 LED arrays, to accommodate larger numbers and messages, or more be a single LED array only. Alternatively, the display may comprise any form of electronic display suitable for displaying a number and/or a message, for example, the display may be an array of LED pixels, an LCD or e-paper screen, or a split-flap display. The display may be arranged in a peripheral module which is separate from the case. The display module may be connected to electrics system with a wired or wireless connection. The electronics system may comprise any display driver which is suitable for chosen display.

The display may be configured to provide further status information, or more detail, in the form of text messages on the display. For example, the display may provide a visual reminder that the scheduled dosing time is due by showing a reminder message in addition to, or instead of, flashing the number 00. The output of the number 00 is an example of a reminder message. The display may be controlled to show the number of injectors remaining in the packaging assembly. The processor arrangement may be configured to determine the number of injectors according to an input from an injector sensor. Alternatively, the processor arrangement may be configured to monitor the number of times that a scheduled dosing time has passed. The display may be controlled to show a notification message when the packaging assembly is empty.

The processor arrangement may be configured to deactivate the display of the user interface if the lid of the case is closed. The processor arrangement may activate the LED based on the fridge open sensor, to indicate to the user that the status of the packaging assembly is normal, when the number of days remaining is greater than one, whether the lid is closed or not. The user may open the lid to activate the display and show the number of days if required. When the scheduled dosing time is due, the processor arrangement may activate both the LED and the display to flash, in order to provide a visual reminder, whether the lid is open or not.

More than one LED may be included in the user interface to indicate the status of the packaging assembly in more detail. For example, a status LED having a first colour may be activated when the number of days until the scheduled dosing time is greater than one, the status LED may flash when the number of days remaining is one day, and a second LED having a second colour may be activated when the scheduled dosing time is due. Alternatively, a single two-colour LED may be used. Alternatively, any other form of notification light or visual output transducer may be used in place of the LED.

A plurality of LEDs corresponding to the plurality of openings may be provided with the packaging assembly of any embodiment. The LEDs may be controlled as described with respect to the fourth embodiment. Alternatively, the processor arrangement may flash or blink one of the plurality of LEDs, while the remaining LEDs are off or illuminated continuously. A different LED may be controlled to blink each time, to guide the user to the next injector for use. One LED may be flashed in a different colour. The processor arrangement may control a number of LEDs according to the number of injection devices remaining in the packaging assembly.

The speaker may be any suitable form of audio output transducer, for example, an electro-acoustic transducer, a piezoelectric buzzer, a moving diaphragm speaker, or a mechanical bell. A vibrating alert may be used instead of or in addition to the audio output transducer.

The fridge open sensor may comprise a phototransistor or, alternatively, a photoresistor or photodiode. Alternatively, the fridge open sensor may comprise a mechanical switch. The fridge open sensor may be located externally from the case and may be positioned at a hinge or frame of the fridge door. The fridge open sensor may be a mechanical switch which is arranged to be pressed by the fridge door in a closed position.

Alternative countdown timer implementations include off-chip and on-chip state-based logic circuits with clock devices, and other forms will be apparent to the skilled person.

The PCB and components of the electronics system may be sealed for protection. For example, the PCB may be coated on each side with a water resistant lacquer or another suitable coating. The electronics system may be coated for protection from moisture or humidity in the interior of a household fridge.

The packaging assembly may include a greater or smaller number of batteries, according to the power requirements of the electronics system. For example, the packaging assembly may include a single battery power pack. The battery or batteries may be removable and replaceable, or may be fixed within the case of the packaging assembly. Alternatively, the packaging assembly may be adapted for a mains power supply, or any alternative power supply.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary). The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing.

Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(w-carboxyheptadecanoyl)-des(B30) human insulin and B29-N-(ω-carboxyhepta-'decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A packaging assembly comprising:
   a case configured to at least partially contain a plurality of injection devices for delivering a medicament;
   a light sensor on the case, the light sensor being configured to detect light incident on the packaging assembly;
   a countdown timer on the case, the countdown timer being configured to monitor a time remaining to a scheduled dosing time for removing an injection device from the case and injecting a medicament; and
   a status indicator on the case, the status indicator being configured to generate an output which indicates a status of the countdown timer conditional on an intensity of light detected by the light sensor exceeding a threshold light intensity,
   wherein the status indicator is activated in response to the detected intensity of light exceeding the threshold light intensity, and is deactivated in response to the detected intensity of light being below the threshold light intensity.

2. The packaging assembly of claim 1, further comprising a reset input device and wherein the packaging assembly is configured to respond to operation of the reset input device by a user to set the scheduled dosing time.

3. The packaging assembly of claim 2, wherein the packaging assembly is configured to respond to operation of the reset input device by a user to set the scheduled dosing time to 14 or 28 days.

4. The packaging assembly of claim 1, wherein the status indicator comprises an audio output transducer; and
   the audio output transducer is configured to generate an audio reminder output to indicate that the scheduled dosing time has been reached conditional on the intensity of light detected by the light sensor exceeding the threshold light intensity.

5. The packaging assembly of claim 1, wherein the status indicator comprises an optical transducer; and
   the optical transducer is configured to generate a visual output to indicate the status of the countdown timer.

6. The packaging assembly of claim 5, wherein the optical transducer comprises a notification light; and
   the notification light is activated at the scheduled dosing time to generate a visual reminder output conditional on the intensity of light detected by the light sensor exceeding the threshold light intensity.

7. The packaging assembly of claim 5, wherein the optical transducer comprises a display;
   wherein the display is configured to generate an output to show a number of days remaining until the scheduled dosing time.

8. The packaging assembly of claim 7, wherein the display is configured to continuously show the number of days remaining until the scheduled dosing time if the scheduled dosing time has not been reached, and to intermittently show the number of days remaining until the scheduled dosing time when the scheduled dosing time has been reached.

9. The packaging assembly of claim 5, further comprising a door open timer configured to be started in response to detecting that the intensity of light sensed by the light sensor exceeds the threshold light intensity,
   wherein the door open timer is configured to expire after a predetermined time in a range of 1 minute to 10 minutes, and the optical transducer is configured to generate the visual output only if the door open timer has not expired.

10. The packaging assembly of claim 1, wherein the status indicator is configured to generate an output which indicates that a state of charge of batteries included in the packaging assembly is below a threshold state of charge.

11. The packaging assembly of claim 1, further comprising:
    a lid coupled to the case and movable between an open position and a closed position; and
    a sensor configured to output a signal representative of a change in position of the lid from the closed position to the open position;
    wherein at least one output of the status indicator is configured to deactivate based on the signal received from the sensor.

12. The packaging assembly of claim 11, wherein at least a portion of the lid is transparent.

13. The packaging assembly of claim 11, wherein the sensor is an electromechanical switch arranged within the packaging assembly such that a state of the electromechanical switch changes between open and closed states as the lid is moved from the closed position to the open position.

14. The packaging assembly of claim 1, further comprising an injection device of the plurality of injection devices, the injection device comprising at lease one dose of the medicament.

15. A method of operating a packaging assembly, comprising:
- receiving a signal from a light sensor on a case of the packaging assembly, the signal being representative of an intensity of light incident on the packaging assembly;
- determining a time remaining on a countdown timer to a scheduled dosing time for removing an injection device from the packaging assembly and injecting a medicament, the countdown timer being on the case of the packaging assembly;
- activating, in response to the intensity of the incident light exceeding a threshold light intensity, a status indicator on the case of the packaging assembly to generate an output which indicates a status of the countdown timer; and
- deactivating the status indicator in response to the intensity of the incident light being below the threshold light intensity.

16. The method of claim 15, further comprising receiving a signal from a reset input device; and
- setting the scheduled dosing time in response to receiving the signal from the reset input device.

17. The method of claim 16, wherein setting the scheduled dosing time comprises setting the scheduled dosing time to 14 days.

18. The method of claim 15, wherein activating the status indicator comprises generating an audio reminder output to indicate that the scheduled dosing time has been reached conditional on the intensity of the light incident on the packaging assembly exceeding the threshold light intensity.

19. The method of claim 15, further comprising starting a door open timer in response to detecting that the intensity of the light incident on the packaging assembly exceeds the threshold light intensity; wherein activating the status indicator to generate the output comprises generating the output only if the door open timer has not expired.

20. The method of claim 15, wherein activating the status indicator to generate the output comprises generating an output which indicates that a state of charge of batteries included in the packaging assembly is below a threshold state of charge.

21. The method of claim 15, further comprising:
- receiving a signal from a sensor representative of a change in position of a lid of the packaging assembly from a closed position to an open position; and
- deactivating at least a part of the generated output based on the signal received from the sensor.

22. The method of claim 21, wherein activating the status indicator to generate the output comprises generating a further output based on the signal received from the sensor, the further output providing information relating to the status of the packaging assembly.

23. The packaging assembly of claim 1, wherein the output generated by the status indicator provides an alert to remove an injection device of the plurality of injection devices from the case at the scheduled dosing time.

24. The method of claim 15, wherein generating the output comprises providing an alert to remove an injection device from the packaging assembly at the scheduled dosing time.

25. The packaging assembly of claim 1, wherein the time remaining on the countdown timer to the scheduled dosing time comprises one or more days.

26. The method of claim 15, wherein the time remaining on the countdown timer to the scheduled dosing time comprises one or more days.

* * * * *

UNITED STATES PATENT AND TRADEMARK OFFICE
CERTIFICATE OF CORRECTION

| | |
|---|---|
| PATENT NO. | : 11,103,632 B2 |
| APPLICATION NO. | : 15/779657 |
| DATED | : August 31, 2021 |
| INVENTOR(S) | : Hardy Kietzmann, Fred Luck and Stefan Riebel |

It is certified that error appears in the above-identified patent and that said Letters Patent is hereby corrected as shown below:

In the Claims

Column 38, Line 66, Claim 14, delete "lease" and insert -- least --

Signed and Sealed this
Seventh Day of December, 2021

Drew Hirshfeld
*Performing the Functions and Duties of the
Under Secretary of Commerce for Intellectual Property and
Director of the United States Patent and Trademark Office*